United States Patent
Noked

(10) Patent No.: US 11,504,006 B2
(45) Date of Patent: Nov. 22, 2022

(54) NON-INVASIVE IMAGING SYSTEMS AND METHODS OF USE

(71) Applicant: Ori Imaging, Inc., Brookline, MA (US)

(72) Inventor: Ori Noked, Brookline, MA (US)

(73) Assignee: Ori Imaging, Inc., Brookline, MA (US)

(*) Notice: Subject to any disclaimer, the term of this patent is extended or adjusted under 35 U.S.C. 154(b) by 0 days.

(21) Appl. No.: 17/384,335

(22) Filed: Jul. 23, 2021

(65) Prior Publication Data

US 2022/0022754 A1     Jan. 27, 2022

Related U.S. Application Data

(60) Provisional application No. 63/055,692, filed on Jul. 23, 2020, provisional application No. 63/055,707, filed on Jul. 23, 2020.

(51) Int. Cl.
*A61B 5/00* (2006.01)

(52) U.S. Cl.
CPC .......... *A61B 5/0082* (2013.01); *A61B 5/4848* (2013.01)

(58) Field of Classification Search
None
See application file for complete search history.

(56) References Cited

U.S. PATENT DOCUMENTS

| | | | |
|---|---|---|---|
| 2015/0190649 A1* | 7/2015 | Gelfand | A61N 5/0601 607/92 |
| 2021/0260399 A1* | 8/2021 | Kariguddaiah | A61F 5/0102 |

OTHER PUBLICATIONS

Tafur et al., "Biophoton Detection and Low-Intensity Light Therapy: A Potential Clinical Partnership". Photomedicine and Laser Surgery, vol. 28, No. 1, 2010, pp. 23-30. (Year: 2010).*

Cifra et al., "Ultra-weak photon emission from biological samples: definition, mechanisms, properties, detection and applications" Journal of Photochemistry and Photobiology B: Biology 139 (2014) 2-10. (Year: 2014).*

* cited by examiner

Primary Examiner — Yi-Shan Yang
(74) Attorney, Agent, or Firm — Greenberg Traurig, LLP

(57) ABSTRACT

Some embodiments of the present disclosure are directed to ultraweak photon emission imaging systems and methods. In some embodiments, a method comprises acquiring an ultraweak photon emission image of a target area of a patient for detection of a pathological condition; wherein the target area comprises an area of interest and a portion surrounding the area of interest, wherein acquiring the image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes so as to achieve a total power output from 1 mW to 10,000 W using an average power density from 0.1 W/cm² to 1 W/cm²; and imaging the target area, wherein imaging the target area comprises a total exposure time from 1 second to 60 minutes.

8 Claims, 10 Drawing Sheets

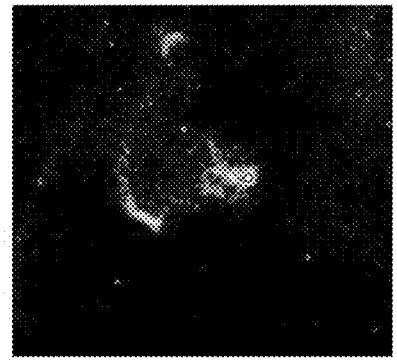 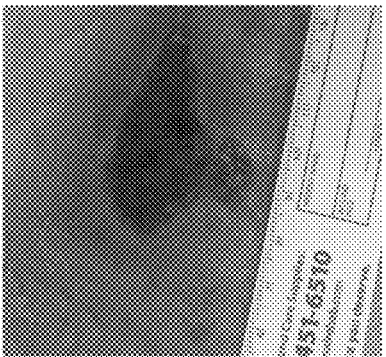 
FIGURE 10A  FIGURE 10B  FIGURE 10C
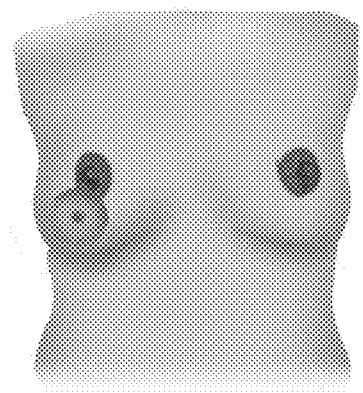 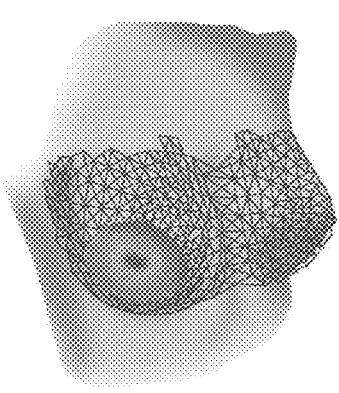 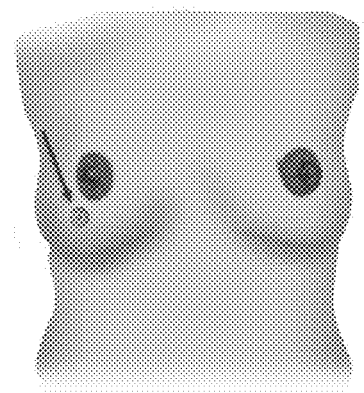
FIGURE 11A  FIGURE 11B  FIGURE 11C

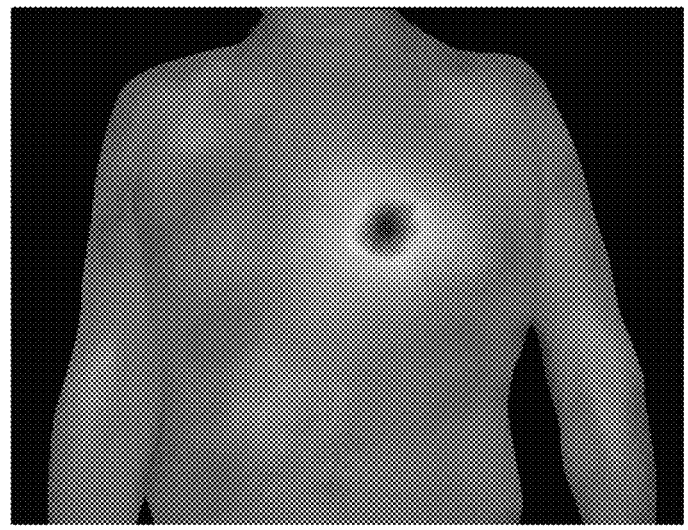
FIGURE 12
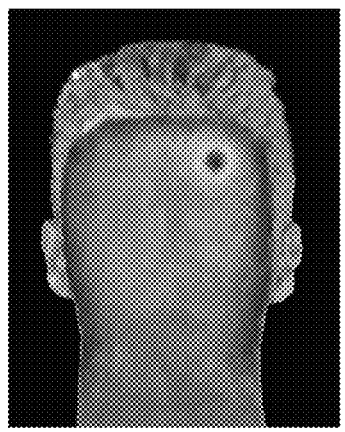    
FIGURE 13A                FIGURE 13B

 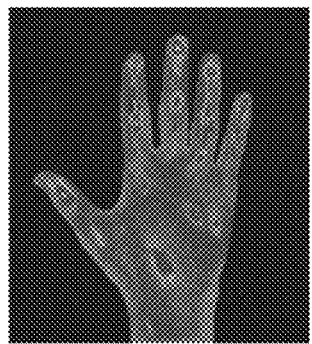
FIGURE 14A　　　　FIGURE 14B
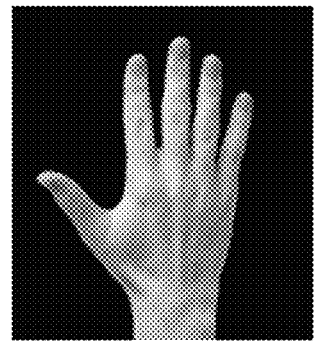 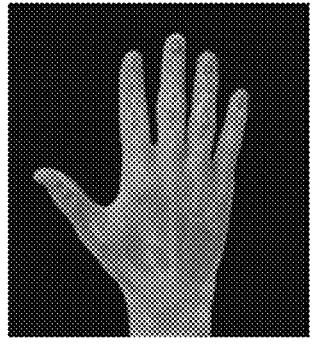
FIGURE 14C　　　　FIGURE 14D
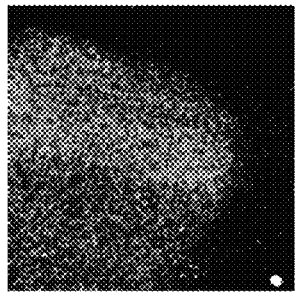 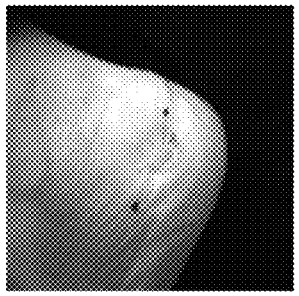 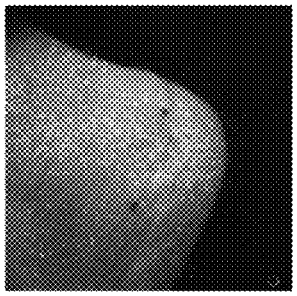 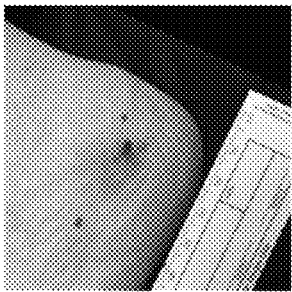
FIGURE 15A　　FIGURE 15B　　FIGURE 15C　　FIGURE 15D

NON-INVASIVE IMAGING SYSTEMS AND METHODS OF USE

FIELD

The embodiments of the present inventions relate to medical imaging devices and methods of use thereof.

BACKGROUND

Medical imaging can be used to detect, analyze, diagnose, prognose and monitor pathological conditions, to recommend, support, guide and assess the efficacy of medical treatment regimen.

SUMMARY OF INVENTION

This summary is a high-level overview of various aspects of the invention and introduces some of the concepts that are further detailed in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification, any or all drawings, and each claim.

Some embodiments of the present disclosure relate to a method. In some embodiments, the method comprises acquiring an ultraweak photon emission image of a target area of a patient for detection of a pathological condition; wherein the target area comprises an area of interest and a portion surrounding the area of interest, wherein acquiring the image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes so as to achieve a total power output from 1 mW to 10,000 W using an average power density from 0.1 W/cm$^2$ to 1 W/cm$^2$; and imaging the target area, wherein imaging the target area comprises a total exposure time from 1 second to 60 minutes.

In some embodiments, applying low level light illumination comprises using a plurality of illumination sources.

In some embodiments, applying low level light illumination comprises applying a continuation light wave.

In some embodiments, applying low level light illumination comprises applying a pulsed light wave.

In some embodiments, the low level light illumination comprises wavelengths from 600 nm to 1100 nm.

In some embodiments, the method comprises applying red light illumination to the target area from 1 second to 5 minutes.

In some embodiments, the method comprises applying white light illumination to the target area from 1 second to 1 minute.

In some embodiments, enhancing formation of the reactive oxygen species and/or the reactive nitrogen species in the target area comprises applying cryotherapy, thermal therapy, fluidotherapy, hydrotherapy, ultrasound, heat lamp, diathermy, or any combination thereof to the target area.

Some embodiments of the present disclosure are directed to a method of treating a chronic wound. In some embodiments, the method comprises obtaining a sufficient amount of at least one medication for treating a chronic wound based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the at least one medication for treating the chronic wound, wherein the medication for treating the chronic wound is selected from group consisting of topical antibacterial, regenerative stem cells therapy, enzymes, growth factors, photodynamic treatment, or any combination thereof; and administering the sufficient amount of at least one medication to treat the chronic wound.

In some embodiments, applying low level light illumination to the target area comprises achieving a total power output from 1 mW to 10,000 W using an average power density from 0.1 W/cm$^2$ to 1 W/cm$^2$.

Some embodiments of the present disclosure relate to a method for treating a chronic wound. In some embodiments, the method comprises obtaining at least one dressing for treating a chronic wound based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the at least one dressing for treating the chronic wound, wherein the dressing for treating the chronic wound is selected from group consisting of hydrogels, hydrocolloids, alginates, foam, silver impregnated dressings, artificial skin, non-adherent dressing, wet to dry dressing, silicon impregnated atraumatic dressings, transparent film dressings, vacuum aided devices, negative pressure dressings, or any combination thereof; and administering at least one dressing to treat the chronic wound.

Some embodiments of the present disclosure are directed to a method of treating a chronic wound. In some embodiments, the method comprises obtaining at least one debridement treatment for treating a chronic wound based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the at least one debridement treatment for treating the chronic wound, wherein the debridement treatment for treating the chronic wound is selected from group consisting of surgical or sharp, autolytic, mechanical, chemical or enzymatic, maggot-based debridement, or any combination thereof; and administering at least one debridement treatment to treat the chronic wound.

Some embodiments of the present disclosure relate to a method of treating a chronic wound. In some embodiments, the method comprises obtaining a chronic wound reducing surgery for treating a chronic wound based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the chronic wound reducing surgery, wherein the surgery for treating the chronic wound is selected from group consisting of Mohs micrographic surgery, partial amputation, corrective surgery, plastic surgery, vascular surgery, or any combination thereof; and administering the chronic wound reducing surgery to treat the chronic wound.

Some embodiments of the present disclosure are directed to a method of treating a chronic wound. In some embodiments, the method comprises obtaining at least one complementary therapy for treating a chronic wound based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the at least one complementary therapy for treating the chronic wound, wherein the complementary therapy for treating the chronic wound is selected from group consisting of hyperbaric oxygen treatment, low-level light therapy, ultrasound therapy, or any combination thereof; and administering at least one complementary therapy to treat the chronic wound.

Some embodiments of the present disclosure relate to a method of treating cancer. In some embodiments, the method comprises obtaining a cancer reducing drug for treating cancer based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cancer reducing drug, wherein the cancer reducing drug is selected from group consisting of chemotherapy, immunotherapy, hormone therapy, targeted drug therapy, radiopharmaceuticals, photodynamic treatment, or any combination thereof; and administering the cancer reducing drug to treat the cancer.

Some embodiments of the present disclosure relate to a method of treating cancer. In some embodiments, the method comprises obtaining a cancer reducing surgery for treating cancer based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cancer reducing surgery, wherein the cancer reducing surgery, is selected from group consisting of biopsy, staging, debulking, tumor removal, also called curative or primary surgery, or any combination thereof; and administering the cancer reducing surgery to treat the cancer.

Some embodiments of the present disclosure are directed to a method of treating cancer. In some embodiments, the method comprises obtaining a cancer reducing radiation therapy for treating cancer based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cancer reducing radiation therapy, wherein the cancer reducing redacting radiation therapy, is selected from group consisting of external beam radiation therapy, internal radiation therapy or any combination thereof; and administering the cancer reducing radiation therapy to treat the cancer.

Some embodiments of the present disclosure relate to a method of treating cancer. In some embodiments, the method comprises obtaining a cancer reducing ablation therapy for treating cancer based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cancer reducing ablation therapy, wherein the cancer reducing redacting ablation therapy, is selected from group consisting of cryoablation, thermal ablation, optical ablation, radiofrequency ablation, thermo-mechanical ablation, focused ultrasound ablation, or any combination thereof; and administering the cancer reducing ablation therapy to treat the cancer.

Some embodiments of the present disclosure relate to a method of treating cardiovascular diseases. In some embodiments, the method comprises obtaining a drug for treating cardiovascular diseases based on an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cardiovascular diseases reducing drug, wherein the cardiovascular diseases reducing drug is selected from group consisting of anticoagulants, aldosterone inhibitors, antiplatelet agents and dual antiplatelet therapy, angiotensin-converting enzyme (ACE) inhibitors, angiotensin II receptor blockers, angiotensin receptor-neprilysin inhibitors, beta blockers, calcium channel blockers, cholesterol-lowering medications, digoxin, digitalis preparations, diuretics, inotropic therapy, proprotein convertase subtilisin kexin type 9 (PCSK9) inhibitors, vasodilators, anti-inflammatory drugs, or any combination thereof; and administering the cardiovascular disease reducing drug to treat the cardiovascular diseases.

Some embodiments of the present disclosure relate to a method of treating cardiovascular diseases. In some embodiments, the method comprises obtaining a minimally invasive operation treatment for treating cardiovascular diseases based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the cardiovascular diseases reducing minimally invasive operation, wherein the cardiovascular diseases reducing minimally invasive operation is selected from group consisting of anticoagulant therapy, coronary angioplasty, keyhole surgery, robotic surgery, coronary artery bypass grafting, endarterectomy, hybrid therapies, or any combination thereof; and administering the cardiovascular disease reducing minimally invasive operation to treat the cardiovascular diseases.

Some embodiments of the present disclosure relate to a method of treating neurological disorders. In some embodiments, the method comprises obtaining a neurological disorder reducing drug for treating neurological disorder based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the neurological disorder reducing drug, wherein the neurological disorder reducing drug is selected from group consisting of analgesics, anesthetics, anorexiants, anticonvulsants, antipyretics, antiemetic/antivertigo agents, antiparkinson agents, anxiolytics, sedatives, and hypnotics, cholinergic agonists, cholinesterase inhibitors, CNS stimulants, drugs used in alcohol dependence, general anesthetics, melatonin, miscellaneous central nervous system agents, muscle relaxants, neuromuscular blockers, neuroprotective agents, parasympathomimetics, psychoactive drugs, sympathomimetics, nervous system drug stubs, VMAT2 inhibitors, or any combination thereof; and administering the neurological disorder reducing drug to treat the neurological disorder.

Some embodiments of the present disclosure relate to a method of treating neurological disorders. In some embodiments, the method comprises obtaining a neurological disorder reducing surgery for treating neurological disorder based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the neurological disorder reducing surgery, wherein the neurological disorder reducing surgery is selected from group consisting of cerebrovascular surgery including aneurysms and arteriovenous malformations (AVMs), and stroke, neuro-oncology, spinal neurosurgery, functional and epilepsy neurosurgery, general neurosurgery, skull base surgery, trigeminal neuralgia and nerve compression syndromes, peripheral nerve injury, deep brain stimulation, radiosurgery, minimally invasive surgery, or any combination thereof; and administering the neurological disorder reducing surgery to treat the neurological disorder.

Some embodiments of the present disclosure relate to a method of treating neurological disorders. In some embodiments, the method comprises obtaining a complementary therapy for treating neurological disorder based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the neurological disorder reducing complementary therapy, wherein the neurological disorder reducing complementary therapy is selected from group consisting of cerebrovascular surgery including hyperbaric oxygen treatment, low level light therapy, nutrition, or any combination thereof; and administering the neurological disorder reducing complementary therapy to treat the neurological disorder.

Some embodiments of the present disclosure relate to a method of treating arthritis and other rheumatic conditions. In some embodiments, the method comprises obtaining an arthritis and other rheumatic conditions reducing drug for treating arthritis and other rheumatic conditions based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the arthritis and other rheumatic conditions reducing drug, wherein the arthritis and other rheumatic conditions reducing drug is selected from group consisting of nonsteroidal anti-inflammatory drugs, counterirritants, anti-inflammatory drugs, disease-modifying antirheumatic drugs, biologic response modifiers, steroidal drug including but not limited to corticosteroids, Janus Kinase (JAK) inhibitors, or any combination thereof; and administering the arthritis and other rheumatic conditions reducing drug to treat the arthritis and other rheumatic conditions.

Some embodiments of the present disclosure relate to a method of treating arthritis and other rheumatic conditions. In some embodiments, the method comprises obtaining an arthritis and other rheumatic conditions reducing surgery for treating arthritis and other rheumatic conditions based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the arthritis and other rheumatic conditions reducing surgery, wherein the arthritis and other rheumatic conditions reducing surgery is selected from group consisting of joint repair, replacement, fusion, realigning bones, lubrication injections, transcutaneous electrical nerve stimulation, or any combination thereof; an administering the arthritis and other rheumatic conditions reducing surgery to treat the arthritis and other rheumatic conditions.

Some embodiments of the present disclosure relate to a method of treating arthritis and other rheumatic conditions. In some embodiments, the method comprises obtaining a complementary therapy for treating arthritis and other rheumatic conditions based on: an acquired ultraweak photon emission image of a target area of a patient; wherein the target area comprises an area of interest and a portion surrounding the area of interest, wherein acquired the ultraweak photon emission image comprises: enhancing formation of reactive oxygen species and/or reactive nitrogen species in the target area, wherein enhancing formation of the reactive oxygen species and/or the reactive nitrogen species comprises applying low level light illumination to the target area from 1 second to 60 minutes, and imaging the target area, wherein imaging the target area comprises a total exposure time from 1 second to 60 minutes; a measured amount of ultraweak photon emission in area of interest in the acquired image of the target area; and a correlation of the measured amount of ultraweak photon emission in the area of interest of the target area to the arthritis and other rheumatic conditions reducing complementary therapy, wherein the arthritis and other rheumatic conditions reducing surgery is selected from group consisting of physical therapy, occupational therapy, low level light therapy, nutrition, or any combination thereof; and administering the arthritis and other rheumatic conditions reducing surgery to treat the arthritis and other rheumatic conditions.

Some embodiments of the present disclosure relate to systems and methods for using ultraweak photon emission (UPE) imaging to measure oxidative stress in humans; analyze imaging data for detection, analysis, diagnosis, prognosis, and/or monitoring pathological conditions; support medical treatment by detecting and monitoring pathological conditions, guiding treatment; and assessing the efficacy of an applied treatment.

In some embodiments, UPE imaging is acquired in a passive approach, without any enhancement mechanism.

In some embodiments, the method includes steps of enhancing UPE, including but not limited to, application of low-level light illumination (LLLI) prior to the UPE imaging. In some embodiments, the method includes additional analysis to UPE imaging, including but not limited to surface map reconstruction, and/or signal reconstruction, and/or incorporating into the analysis other imaging modalities.

In some embodiments, the method includes using an LLLI procedure on a target area and using a highly sensitive detector and optical equipment to measure the UPE of the target area. In some embodiments, the measurement may include a long exposure to measure the UPE of the target area.

In some embodiments, the method includes processing of the UPE image to remove noise, correct background, apply a smoothing algorithm; identifying contours and hot spots by defined thresholds; applying signal reconstruction algorithms to retrieve optical-spatial details of a deep tissue hot spot; and/or merging multiple UPE images to provide depth and spatial analysis of the pathological condition.

In some embodiments, the target area includes at least a portion of an area of interest, and a portion of an area around the area of interest. In some embodiments, the area of interest may be the whole body, the head and neck, part of the head and neck, the torso, part of the torso, the abdomen, part of the abdomen, and/or any organ in the body, including but not limited to, stomach, intestines, liver, gallbladder, pancreas, thyroid, lung, kidney, bladder, ovary, uterus, testicle, prostate, heart, artery or vein, lymph node, bone, bone marrow, muscle, joint, tendon, spleen, brain, brainstem, cerebellum, spine and spinal cord, connective tissue, or other.

In some embodiments, the pathological conditions may primarily be conditions which are manifested by oxidative stress. In some embodiments, the pathological conditions may be cancer tumors or metastases in any part of the body, ischemia and/or ischemia/reperfusion, cardiovascular diseases, neurological diseases, diabetes and related conditions, arthritis or other rheumatic conditions, traumatic injuries, autoimmune diseases, any condition which manifests inflammation, infections from bacterial, fungal, viral, or parasitic sources, and other diseases.

In some embodiments, the pathological conditions may be chronic wounds, including but not limited to diabetic (foot) ulcer, venous stasis ulcer, pressure ulcer, burn, vasculitic (leg) ulcer, and post-operative infection. In some embodiments, the pathological conditions may be, but not limited to, malignant wounds of a primary cancer or a metastasis to the skin from a local tumor or from a tumor in a distant site. In some embodiments, the pathological conditions may be, but not limited to, acute wounds, such as traumatic wounds or surgical wounds. In some embodiments, the pathological conditions may be, but not limited to, skin and soft tissue infections from bacterial, fungal, viral, or parasitic sources.

Embodiments of the present disclosure also relate to systems and methods for using UPE-analyzed images for early detection of pathological conditions to allow for early intervention. The systems and methods may include using UPE-analyzed images of the same patient and the same area of interest, taken at different times, in a comparison and contrast analysis to provide guidance for treatment and assess the efficacy of treatment; using UPE-analyzed images as control benchmarks, for example from UPE-analyzed images from different patients with similar or different pathological conditions, as well as from UPE-analyzed images of healthy individuals; using UPE-analyzed images and derived control benchmarks to improve algorithms for analysis, diagnosis, prognosis, as well as treatment guidance and efficacy assessment.

Some embodiments of the present disclosure also relate to systems and methods for producing LLLI by light emitting diode (LED), organic LED (OLED), solid state laser, gas laser, diode laser, incandescent lamp, halogen light source or other light sources. In some embodiments, the LLLI emitted light passes through a filter, before reaching the patient, including but not limited to, short or low pass, high or long pass, band pass, band stop, polarizer, and any combination thereof. In some embodiments, the LLLI may include one, two or more sources, including but not limited to, the same type of illumination source, or different types of illumination sources.

In some embodiments, the LLLI is a continuous wave (CW).

In some embodiments, the LLLI is a pulsed wave (PW) and the LLLI pulse structure, including the pulse peak [W], the pulse width [second] and the duty cycle (DC) [%] may vary. In some embodiments, the LLLI wavelength may vary in the range of 600-1100 nm. In some embodiments, the LLLI may include one, two or more wavelengths at the same time (with a spectral width around each central emission wavelength), from one, two or more sources. In some embodiments, the LLLI may vary in its irradiance [W/cm$^2$], irradiance time [second] and therefore vary in the total fluence [J/cm$^2$], and energy [J].

In some embodiments, the LLLI may be applied in contact with the skin without indentation in the skin, in contact with the skin with a small indentation in the skin, or at any distance from the skin. In some embodiments, the LLLI may be applied from every direction with respect to the patient's body.

In some embodiments, the LLLI is applied through an optical waveguide, including but not limited to an optical fiber. In some embodiments, the waveguide can be placed contact with the skin without indentation in the skin, in contact with the skin with a small indentation in the skin, or at any distance from the skin. In some embodiments, the waveguide can be placed inside the body, including but not limited to using a catheter in any cavity in the body. In some embodiments, the LLLI is applied using an internal wireless source including but not limited to a capsule which can be introduced into a static location or changing location, by different means, including but not limited to minimally-invasive surgical insertion, injection, swallowing, or other.

In some embodiments, the UPE image is acquired through no filter or one or more filters, including but not limited to, short or low pass, high or long pass, band pass, band stop, polarizer, and any combination thereof. In some embodiments, a series of UPE images is taken through different filters and/or no filters, and the images are each analyzed individually, as well as compared to and/or contrasted with each other, superimposed and/or displayed. In some embodiments, the filters can be used to provide more detailed spectroscopic data. In some embodiment, different filter technologies can be used, including but not limited to tunable filters.

In some embodiments, the systems and methods further include immobilizing the target area, part of the patient and/or the entire patient.

In some embodiments, the systems and methods further include optical insulation of the target area, the area of interest, part of the patient, the entire patient, and/or part or all the examination room.

In some embodiments, the systems and methods further include alignment of the imaging device to the correct orientation using a dedicated mechanical arm.

In some embodiments, the systems and methods further include placement of the optical detector directly on the skin above the measured body part or at a specific set distance from the skin above the measured body part. The spacing of the detector from the skin can be achieve by a mechanical support module, including but not limited to a rigid or semirigid shape, from any suitable material, which can support the and stabilize the optical detector as well as optically insulate the skin to detector pathway.

In some embodiments, the systems and methods further include use of multiple image acquisitions and/or video of the target area, part of the patient and/or the entire patient to compensate for respiratory and other movements.

In some embodiments, the systems and methods further include movement monitoring of the patient, either caused by breathing or other causes, using different technologies, including but not limited to passive and active infrared thermal imaging, mechanical sensor, acoustic and/or ultrasonic sensor, electromechanical sensor, laser sensor, and radiofrequency wave or microwave sensors. In some embodiments, the systems and methods further include synchronization of the movement monitoring to the measured UPE imaging in order the compensate for the patient's movement.

In some embodiments, the systems and methods further include incorporating red light (RL) illumination with and without filters, images and analyzed images; incorporating white light (WL) illumination with and without filters, images and analyzed images; incorporating three-dimensional (3D) surface reconstruction, incorporating structured light (SL) images and analyzed images; and/or incorporating signal reconstruction algorithms, including but not limited to diffusion-model based algorithms, autocorrelation-based algorithms, combination thereof, or others. In some embodiments, the spatial matching of the UPE imaging onto the surface reconstruction map may provide better visualization for analysis. In some embodiments, the spatially matched UPE imaging can be used as an actionable starting point for signal reconstruction algorithms to retrieve the optical-spatial details of a deep tissue signal.

In some embodiments, the systems and methods may include other superficial imaging modalities, including but not limited to, near infrared imaging or near infrared multispectral imaging (MSI), autofluorescence (AF) imaging, and thermal imaging, which may be used to measure the same target area and/or area of interest.

In some embodiments, the systems and methods may include other imaging modalities, including but not limited to, computed tomography (CT) and magnetic resonance imaging (MRI), which may be used to measure the same target area and/or area of interest.

In some embodiments, the systems and methods further include a medical record system, which records all the acquired images, analyzed images, superimposed images, compare and contrast images, for every measurement, for each patient, in a secured and compliant way. In some embodiments, the systems and methods further include personalized decision support algorithm based on the data collected from all the measurements, and the progression (healing/deterioration) of the pathological condition as a function of time.

BRIEF DESCRIPTION OF THE DRAWINGS

Some embodiments of the present disclosure are herein described, by way of example only, with reference to the accompanying drawings. With specific reference now to the drawings in detail, particulars shown are by way of example and for purposes of illustrative discussion of some embodiments of the invention. In this regard, the description taken with the drawings makes apparent to those skilled in the art how embodiments of the invention may be practiced.

FIG. 5A is an UPE raw data image after noise reduction of a post-operative infected wound in the chest. FIG. 5B is a smoothed UPE image of FIG. 5A. FIG. 5C is a WL illumination color image of the wound. FIGS. 5D and 5E are threshold analysis of the UPE images, with two different threshold levels. FIG. 5F shows the calculated contour and boundaries of the FIG. 5E threshold image.

FIG. 9A is a 2D UPE image of the diabetic foot ulcer with a clear infection hot spot. FIG. 9B is a black and white photo of the wound. FIG. 9C shows FIG. 9A superimposed on FIG. 9B.

FIGS. 10A-C shows an exemplary embodiment of the present disclosure used for venous stasis ulcer on the leg. FIG. 10A is a 2D UPE image. FIG. 10B is a WL illumination color image of the wound. FIG. 10C shows FIG. 10A superimposed on FIG. 10B.

FIGS. 11A-C show an exemplary embodiment of the present disclosure used for the detection of a breast cancer. FIG. 11A is a 2D UPE image of the breast cancer hot spot illustration superimposed on a black and white smoothed photo of a female torso. FIG. 11B is a 3D surface reconstruction of the breasts. FIG. 11C shows the UPE signal reconstruction to the hot spot of the cancer tumor in the breast.

FIG. 12 shows an exemplary embodiment of the present disclosure used for the detection of coronary heart disease.

FIGS. 13A-B show an exemplary embodiment of the present disclosure used for the detection and monitoring of a stroke. FIG. 13A is a 3D UPE image of the head superimposed on a black and white photo of head, retrieved from two cameras. FIG. 13B is the UPE signal reconstruction to the hot spot of the stroke, based on 3D surface reconstruction and the UPE images, shown via two angles: front and side view.

FIGS. 14A-D show an exemplary embodiment of the present disclosure on a hand of a patient suffering from rheumatoid arthritis. FIG. 14A is an UPE image taken without LLLI. FIG. 14B is an UPE image taken after LLLI. FIG. 14C is a black and white photo of the hand, and FIG. 14D is a superimposed image of the LLLI enhanced UPE image (FIG. 14B) on the black and white photo of the hand (FIG. 14C).

FIGS. 15A-D show an exemplary embodiment of the present disclosure used as a control measurement of a wound that healed well in the patient's heel. FIG. 15A is a 2D UPE image of the heel. FIG. 15B is a black and white photo of the heel. FIG. 15C shows FIG. 15A superimposed on FIG. 15B. FIG. 15D is a WL illumination color image of the patient's heel and the wound that healed well.

DETAILED DESCRIPTION

Figure 1:
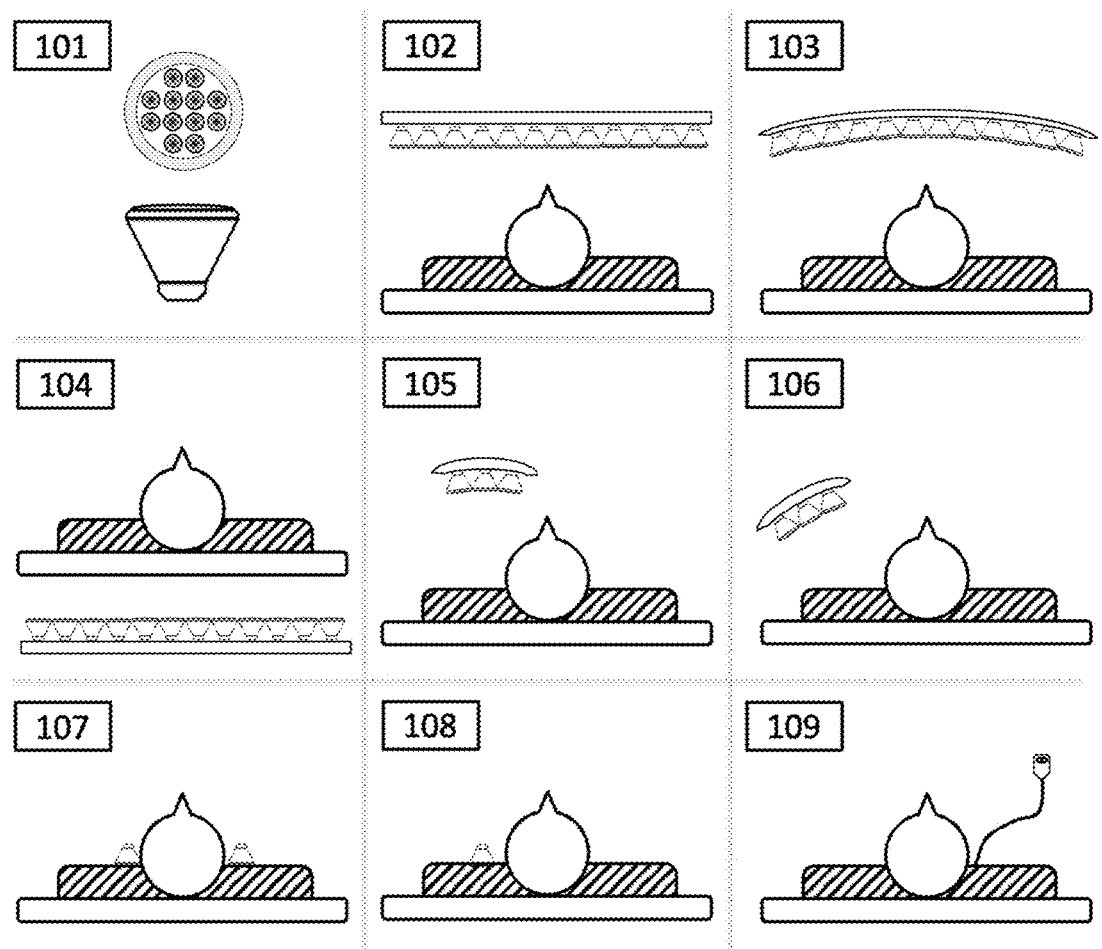
FIG. 1 is an illustration of LLLI embodiments, including different designs and orientations.

The following description of the preferred embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by referenced in their entireties. In the event of a conflict between a definition in the present disclosure and that of a cited reference, the present disclosure prevails.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention.

Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," "mounted" and similar refer to a relationship wherein structures are secured or attached to one another either directly or indirectly through intervening structures, as well as both movable or rigid attachments or relationships, unless expressly described otherwise.

As used in the specification and the claims, the singular form of "a", "an", and "the" include plural referents unless the context clearly dictates otherwise.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The terms "first", "second", and the like are not intended to refer to any particular order or chronology, but instead refer to different conditions, properties, or elements.

All documents referred to herein are "incorporated by reference" in their entirety.

The term "at least" means "greater than or equal to". The term "not greater than" means "less than or equal to".

The exemplary embodiments of the present disclosure will be further explained with references to the attached drawings. The drawings are schematic and illustrative in nature and are not necessarily to scale, without specific intensity bars, and provide only one version of one exemplary embodiment of the present disclosure.

As used herein, "pathological conditions" refers to any medical condition at any place and/or depth in the human body, which may be manifested by oxidative stress. In some embodiments, the pathological conditions may be medical conditions in the skin ranging from the surface of the skin to a depth of about 5 mm from the surface of the skin. In some embodiments, the pathological conditions may be medical conditions which manifest deeper than the skin. In some embodiments, the pathological conditions may be medical conditions which manifest both in the skin and deeper than the skin.

As used herein, "target area" refers to the entire area recorded by the imaging system, which means the full frame, including parts of the image with nothing but background.

As used herein, "measurement" refers to the use of at least one modality during one continuous time frame. That means that the use of more than one modality in sequence to another modality is still within the same measurement and the modalities should be effectively co-registered, assuming the imaging modalities are integrated, and the patient is stationary.

As used herein, "image", refers to two dimensional (2D) raw data produced by any imaging modality. These include images produced with any type of illumination, filtering, and exposure duration or any other imaging parameter.

As used herein, "analyzed image" refers to an image that went through at least one image processing procedure.

As used herein, "area of interest" refers to an area with an actual or suspected pathological condition, which is inside the target area. In some embodiments, the target area includes at least a portion of the area of interest and a healthy area around or adjacent to the area of interest.

As used herein, the term "surface reconstruction map" refers to the conversion registration of the target area or the area of interest or any region therein. In some embodiments, the reconstruction map may be the product of 2D structured light images, or equivalent techniques, converted to 3D representation.

As used herein, "region" refers to any area in the target area, which may be completely inside the area of interest, may be completely outside the area of interest, or may be partially inside the area of interest and partially outside the area of interest. In some embodiments, the region can be the entire target area.

As used herein, the term "threshold" refers to an intensity of a measured signal with a discrimination of the signal above or below it. In some embodiments, the threshold may be used to indicate a region of positive signal and distinguish that region from the rest of the measured target area. In some embodiments, the region will be determined for one or more modalities. In some embodiments, more than one threshold level will be used (i.e. multilevel threshold).

As used herein, the term "contour" refers to an outline of a specific feature in the target area, which may be, but is not limited to, the area of interest. In some embodiments, the contour will be determined for one or more modalities. In some embodiments, the contour will be the boundary of a region.

As used herein, the term "compare and contrast image" refers to an analysis of two or more images, analyzed images, target area, area of interest, or regions, before or after application of surface reconstruction map, and before or after signal reconstruction, of two or more different measurements. In some embodiments, the two or more different measurements may be of the same patient, using different imaging modalities, and/or separated by time. "Comparing" the two or more modalities and/or two or more measurements refers to finding the overlaps between the two or more modalities and/or two or more measurements and "contrasting" refers to identifying the regions that are not overlapping and differentiating them more clearly from the overlapping parts as well as differentiating the other characteristics between the two embodiments in the overlapping regions in term of, but not limited to, intensity of respective signal, texture, spectral properties, and other.

Some embodiments of the present disclosure relate to systems and methods for using ultraweak photon emission (UPE) imaging to measure oxidative stress in humans. UPE imaging is based on light emission associated with oxidative processes in living organisms. Although the emitted light is too faint to be detected by the eye, every living organism emits light (electromagnetic radiation) primarily in the 300-1300 nm spectral range. This spectral range includes soft ultraviolet 315-400 nm, visible 400-700 nm, and part of the near-infrared (NIR) 700-1300 nm spectrum.

As used herein, the term "enhancement" refers to any process, method, technique, or mechanism used to enhance, boost, induce, amplify, or activate the tissue to increase the measured signal, and/or improve the signal-to-noise (SNR), and/or result in a higher contrast between pathological conditions compared to healthy tissues.

As used herein, the term UPE imaging refers to both UPE imaging done passively, meaning without any prior process, as well as UPE imaging done after any process of enhancement, for example after low-level light illumination.

The amount of light emitted by every living organism is significantly larger than can be explained by thermal emission. This radiation is associated with the formation of reactive oxygen species (ROS) and reactive nitrogen species (RNS), or collectively ROS/RNS. These chemical species cause the oxidation of biomolecules, which in turn result in the formation of high-energy intermediates. These intermediate products emit light upon relaxation to the ground state. This light is termed ultra-weak photon emission or UPE. A healthy tissue will exhibit a low-level of UPE, as most of the ROS/RNS will be scavenged by a dedicated antioxidant defense system of the organism. A non-limiting review on UPE emission from living organisms, is disclosed in "Ultra-weak photon emission from biological samples: Definition, mechanisms, properties, detection and applications," by M. Cifra and P. Pospíšil, published in Journal of Photochemistry and Photobiology B: Biology, 139, 2 (2014), which is herein incorporated by reference in its entirety.

Excessive formation of ROS/RNS characterizes the condition known as oxidative stress. It is closely associated with a variety of different pathological states, including cancer, inflammation, infection, cardiovascular diseases, neurological disorders, ischemia/reperfusion, other diseases and ageing. A non-limiting review on free-radicals, oxidative stress and its relation to pathological condition is disclosed in "Free radicals and antioxidants in normal physiological functions and human disease", by M. Valko, D. Leibfritz, J. Moncol, M. T. D. Cronin, M. Mazur, and J. Telser, published in The International Journal of Biochemistry & Cell Biology, 39, 44 (2007), which is herein incorporated by reference in its entirety.

In oxidative stress conditions, the formation of ROS/RNS exceeds the capacity of the defense system, and UPE production is several orders of magnitude higher than normal—e.g., emission of $10^2$-$10^5$ vs. $10^{-1}$-$10^2$ photons/cm$^2$s. UPE production has been measured in plant samples and in a variety of in vitro tissue samples, and in vivo surface diagnostics, using a photomultiplier tube and/or a highly sensitive camera.

Some embodiments of the present disclosure also include systems and methods for enhancing UPE by application of low-level light illumination (LLLI) prior to the UPE imaging as well as systems and methods for producing LLLI by light emitting diode (LED), organic LED (OLED), solid state laser, gas laser, diode laser, incandescent lamp, halogen light source or other light sources. LLLI procedures may be closely related to low-level light therapy (LLLT), also known as photobiomodulation, which is an established field of medical research and practice, where patients are irradiated with low-level (low power) light sources. A non-limiting review on low-level light therapy is disclosed in "Low-level light therapy: photobiomodulation", by M. R. Hamblin, C. Ferraresi, Y. Huang, L. F. de Freitas, and J. D. Carroll, published in SPIE Press, 2018 Series: Tutorial texts in optical engineering, v. TT 115, which is herein incorporated by reference in its entirety.

LLLI works in different ways on the chemical and cellular level. The main mechanism discussed in the literature is absorption of the light by cytochrome c oxidase (CCO), which is a complex IV enzyme in the electron transport chain inside the mitochondria. LLLI increases the activity of complexes I, II, III, and IV and therefore the reduction of molecular oxygen in the catalytic center of CCO, which increases the mitochondrial membrane potential (MMP) and the levels of adenosine triphosphate (ATP), ROS, and nitric oxide (NO). Some other mechanisms and light-absorbing cellular structures have been considered. There are indications that NIR might be absorbed by water near surfaces, which in turn change its viscosity. Lower viscosity allows the mitochondrial rotary motor, ATP synthase, to be more efficient, thereby increasing the electron transport chain activity and upregulating the ATP production. Other downstream processes are also affected by LLLI, through multiple signaling, ion channels, transcription factors, and biosynthetic processes.

The application of LLLI results in a temporary, higher formation of ROS/RNS, which is sometimes referred to as a burst. The short-term burst of ROS/RNS enhances the UPE emission intensity. The enhancement of the UPE signal enables detection of weaker and/or deeper hot spots. Given that the antioxidant system will likely scavenge the additional ROS/RNS more effectively in the healthy tissue compared to the tissue under oxidative stress, the UPE enhancement from the distressed tissue is expected to be higher. Even if the enhancement of the UPE signal from healthy tissue and from the pathological hot spot is comparable, because of the imaging devices' detection limit the additional signal would increase the contrast and enable better detection of the hot spot.

The instant exemplary embodiments concern using UPE imaging to measure oxidative stress in humans, and analyzing the imaging data to detect, analyze, diagnose, prognose, and monitor pathological conditions. The instant exemplary embodiments can enable early detection which may allow for timely interventions, as well as support medical treatment by providing diagnosis and prognosis to recommend and guide treatment, and by assessing the efficacy of the applied medical treatment.

In some embodiments, the UPE spectral properties can be measured, using different filters, and used for diagnostic and prognostic purposes by differentiating between the spectral characteristics of different pathological conditions (e.g. cancer vs. inflammation).

In some embodiments, UPE analyzed images of the same patient and the same area of interest, taken at different times, are compared and contrasted. Such a procedure may allow for direct quantification of a change in the level and distribution of the oxidative stress associated with the pathological condition. The change can be used as a measure for the progression of the disease (healing/deterioration), and/or as an indication for treatment efficacy, for example: anti-inflammatory medication for rheumatoid arthritis, antibiotic treatment for a bacterial infection of a skin wound, hyperbaric oxygen treatment to reduce inflammation in the secondary phase of a traumatic brain injury or to reduce hypoxic conditions in a chronic wound, or other, etc.

In some embodiments, UPE analyzed images of different patients with similar or different pathological conditions can be used to improve algorithms for detection, diagnosis and prognosis, as well as treatment guidance and efficacy assessment.

In some embodiments, UPE imaging is acquired using a passive approach, for example, an approach without any enhancement mechanism prior to the acquisition of the UPE image.

In some embodiments, UPE may be enhanced to acquire the images. The UPE may be enhanced using any method known to those skilled in the art, including, for example, the application of LLLI. In an exemplary embodiment of the present disclosure, LLLI may be configured to enhance the signal emitted by the irradiated tissue, which would increase the measured signal, improve the signal-to-noise (SNR) and result in a higher contrast between pathological conditions compared to healthy tissue. The enhancement of the signal enables detection and characterization of signal from deeper tissues, and reduction of the UPE imaging exposure time.

In some embodiments, other enhancement methods include but not limited to cryotherapy such as ice pack, vapor coolant spray, ice massage, and cold whirlpool; thermal therapy, including conduction-based such as hydrocollator pack, low-level heat wrap, and paraffin bath, convection-based such as fluidotherapy, and hydrotherapy, and conversion-based such as ultrasound, heat lamp, and diathermy; alternating cryotherapy and thermotherapy; and other means to induce non-harmful hormesis.

As discussed herein, LLLI can be produced by using a variety of light sources having illumination properties that include, but are not limited to, to continuous and pulsed sources, with different wavelengths, peak power, pulse width and duty cycle. The illumination properties of the light sources may be optimized to deliver the maximum enhancement of UPE signal, reaching to the deepest relevant tissue depth, at minimum time, without over-heating the irradiated tissue. For example, illumination sources may be chosen to maximize the LLLI energy reaching the target area in the patient, as maximizing the amount of LLLI may maximize the UPE signal emitted from the target area.

In some embodiments, LLLT treatments may be conducted with red or NIR light (600-1100 nm), with a total output power of 1 mW-10,000 W using an average power density that does not heat the tissue (<1 W/cm$^2$, depending on the wavelength and tissue type). For reference, a whole-body skin surface area of an adult is on average 1.5-2 m$^2$, or 15,000-20,000 cm$^2$. In some embodiments, the LLLI is produced by, but not limited to, light emitting diode (LED), organic LED (OLED), solid state laser, gas laser, diode laser, incandescent lamp, halogen light source, or other. In some embodiments, the LLLI emitted passes through a filter, before reaching the patient, including but not limited to, short or low pass, high or long pass, band pass, band stop, polarizer, and any combination thereof. In some embodiments, the LLLI may include one, two or more sources, including but not limited to, the same type of or different types of illumination sources.

FIG. 1 depicts exemplary LLLI embodiments, including different designs and orientations of illumination sources. As shown in FIG. 1, the illumination sources may include, but limited to, one or more light emitting components. An illustrative embodiment of an LED bulb with 12 LEDs is presented in 101. A flat panel of such units located over patient lying supine on a bed is presented in 102 and similar arrangement using a curved panel is illustrated in 103. A flat LLLI panel irradiating from under the bed is demonstrated in 104. A smaller LLLI panel of any size is illustrated illuminating directly down at a patient in 105, or at an angel with respect to the patient in 106. These non-contact embodiments are part of the exemplary embodiment. In some embodiments, the LLLI may be in contact with the skin without indenting the skin 107, using one or more illumination sources. In some embodiments, the LLLI may be in contact the skin with a small indentation in the skin 108. In some embodiments, the LLLI may be in applied to the body from a light source via a waveguide, including but not limited to an optical fiber 109. Practical illumination of large areas would likely require illumination at some distance from the skin. In some embodiments, up to 50% of the light may be reflected back and outside of the patient's body. Therefore, contact illumination may allow the effective transmission of more power, because the light scattering into the body is more efficient. In some embodiments, small indentation into the skin of the illuminating light source may allow for even more efficient scattering of the light into the body. The light diffusion into the body means that the light would penetrate deep and laterally into the tissue, allowing for effective illumination of internal body parts. As shown in FIG. 1, in some embodiments, the LLLI may be applied from every direction with respect to the patient's body.

In some embodiments, the LLLI may include a cooling unit to remove the excess heat from the light emitting components. In some embodiments, the LLLI would be continuous wave (CW). The maximum power in CW mode is limited by excess or over heating of the tissue, which is primarily depended on the wavelength and the tissue type. The power limit effectively depends on the size of the irradiated area. For a point illumination the power can be higher than a wide, or whole body, illumination.

In some embodiments, the LLLI would be pulsed wave (PW). For PW, the LLLI pulse structure, including the pulse peak [W], the pulse width [second] and the duty cycle [%] may vary. The total energy would be the pulse peak times the duty cycle times the illumination time. The limitation on the combination of different parameters would still be avoiding overheating of the tissue. In some embodiments, using PW, more light may be able penetrate deeper into a patient than using CW, because the duty cycle allows for better thermal dissipation. Lower duty cycle can enable higher peak power. Nominally, the peak power would be around 500 mW, with 0.1 second pulse width (10 Hz), and 50% duty cycle.

In some embodiments, the LLLI wavelength may vary in the range of 600-1100 nm. The most spectrally transparent range in human biological tissue, which is many times referred to as the NIR optical window or therapeutic window, overlaps with this spectral range. There are different definitions to the optical window, sometime defines as narrowly as 750-900 nm. Nominally, the LLLI in use, for the deepest tissue applications, would be in the 800-850 nm range. In some embodiments, the LLLI may include one, two or more wavelengths at the same time (with a spectral width around each central emission wavelength), from one, two or more sources.

In some embodiments, the LLLI may vary in its irradiance [$W/cm^2$], irradiance time [second] and therefore vary in the total fluence [$J/cm^2$], and energy [J]. The illumination time is limited by practical constraints. If it is too short, the effect will be too limited. If it is too long, the patient will feel discomfort. While examination can take up to an hour in a scan such as an MRI, for LLLT application illumination time may be in the range of 1 second to 60 minutes, in the range of 1 to 30 minutes, in the range of 5 to 25 minutes, and more preferable in the range of 10-20 min. In an exemplary embodiment of the present disclosure, the following parameters for the illumination source may be used to maximize the UPE signal emitted from a target area: PW, a combination of two sources at 600-650 nm and 800-850 nm, 500 $mW/cm^2$, 0.1 second (10 Hz), 50% DC, for 600 second (10 min), which results in fluence of 150 $J/cm^2$.

Figure 2:
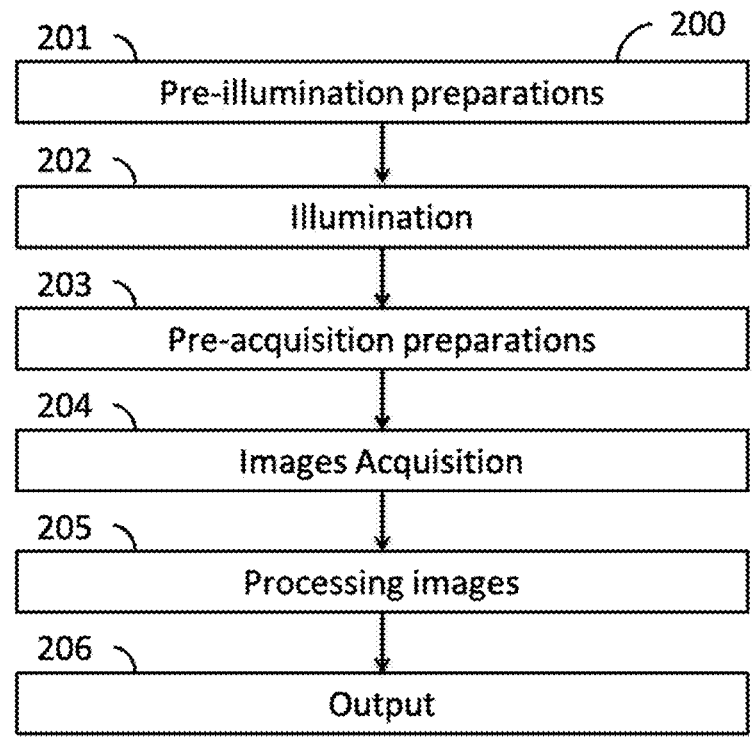
FIG. 2 is a flow chart illustrating an exemplary embodiment of the present disclosure, showing the illumination, imaging, and analysis procedures.

FIG. 2 depicts a flow chart of an exemplary embodiment of the present disclosure, which is a method 200 for obtaining and analyzing a UPE image. As previously discussed, in some embodiments, the method of UPE imaging and analysis is performed by passive UPE imaging, without enhancement. In addition, in some embodiments, including the embodiments discussed in the following description, UPE imaging may follow a LLLI enhancement.

At 201 of the method 200 the preparations of the patient and of the LLLI system take place. Once the pre-illumination preparations are concluded, the patient is illuminated according to the specified LLLI protocol of the embodiment in 202. After the LLLI, the patient and the UPE imaging system are being prepared, in 203, for image acquisition in 204. After gathering all the data, the patient resumes normal function and the data collected in 204 is analyzed in 205 to generate the output of the method 206. The output of the method includes the analysis of the instant exemplary embodiments, as well as of each of the other imaging modalities, either incorporated or physically integrated; superimposing, and compare and contrast analysis of the different imaging modalities of the current measurement, including surface reconstruction and signal reconstruction. In some embodiments, the system is integrated as to allow the smooth transition of the method, particularly 201 to 204 without need for separate adjustment between illumination and imaging.

Figure 3A:
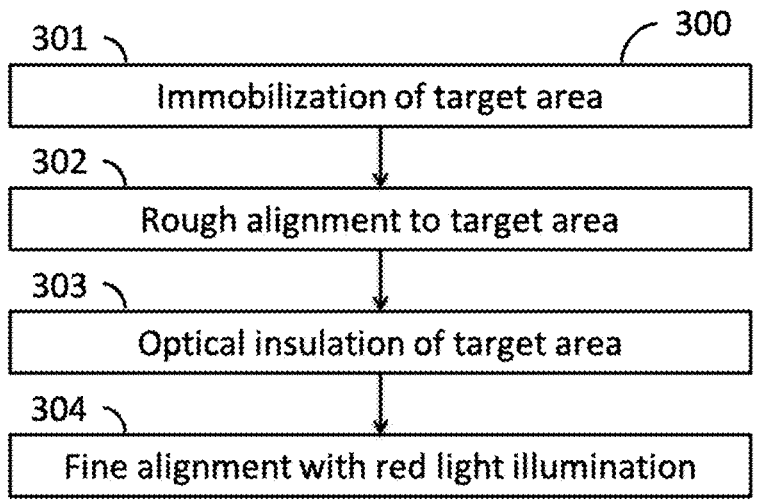
FIGS. 3A and 3B are flow charts illustrating exemplary embodiments of an imaging system procedure prior to imaging (FIG. 3A) and an imaging sequence (FIG. 3B).

FIG. 3A depicts a flowchart of the pre-acquisition preparations (i.e. 203). The first stage is immobilization of the target area 301. The target area can be any part of the body. The relevant body part depends on the pathological condition. In some embodiments, such as wound care, the most relevant body parts may be the lower extremities, lower back or different body parts. In some embodiments, such as neurology the head would be the target area. The method of immobilization will be based on the condition and the body part, which requires immobilization. The immobilization might be, but not limited to, rigid parts such as splints, more flexible parts such as strips, sheets, cushions or any other mechanical arrangement. In some embodiments, the mechanical immobilization if the body part is set with respect to the imaging system, so that a rigid and/or semi-rigid mechanical separator provides support and stabilization for the imaging system to allow imaging of the measured body part, even with small movement of the rest of the body. In some embodiments, the patient might be conscious, partly conscious, or unconscious. In other embodiments, the patient can be requested not to move for duration of the measurement. In some embodiments, a movement correction procedure will be implemented.

Once the target area is immobilized, the optical system may be aligned to measure the target area 302. In some embodiments, this step may occur when the room lights are already OFF, or dimmed, or RL illumination, similar to the RL illumination of the system, in the room is ON. In other embodiments, partial optical insulation is already over the patient and the rough alignment is done with the system RL illumination, which is turned ON. In some embodiments, the rough alignment may be achieved by using the imaging device on video mode, with the proper settings to insure clear smooth video without saturation of the sensor. The alignment includes moving the imaging parts 405, the mechanical arm 402-404, and the system unit 401 (FIG. 4), to enable the best alignment of the optical components and the target area. In some embodiments, the patient's bed or chair can be adjusted as well to help with the alignment process. In some embodiments, the rough alignment may conclude when the target area is all, or at least mostly in focus (optimal focus) and includes at least a portion of the area of interest, and a healthy area around or adjacent to the area of interest. In some embodiments, the system might include fixed focus optical system. In other embodiments, the system might include an adjustable focus optical system.

Following the immobilization of the patient 301 and rough alignment of the optical system to the target area 302, the target area may be optically insulated. In some embodiments, the optical insulation may include insulating part of, or all, the entire exam room. Once the target area is properly optically insulated 303, in some embodiments, it may be required to fine-tune the optical alignment 304 prior to images' acquisition to ensure that nothing has moved during the optical insulation stage and as a double check that the system is ready for the clinical measurement. The fine alignment is similar to the rough alignment and is concluded when the orientation of the optical system is optimized to the target area and the target area is in optical focus. Once these conditions are met, the fine alignment is done, and the system is switched from video mode to image acquisition mode. In some embodiments, mechanical immobilization provides support for the imaging system, including optical alignment (rough alignment, fine alignment, and focus), as well as optical insulation.

Figure 3B:
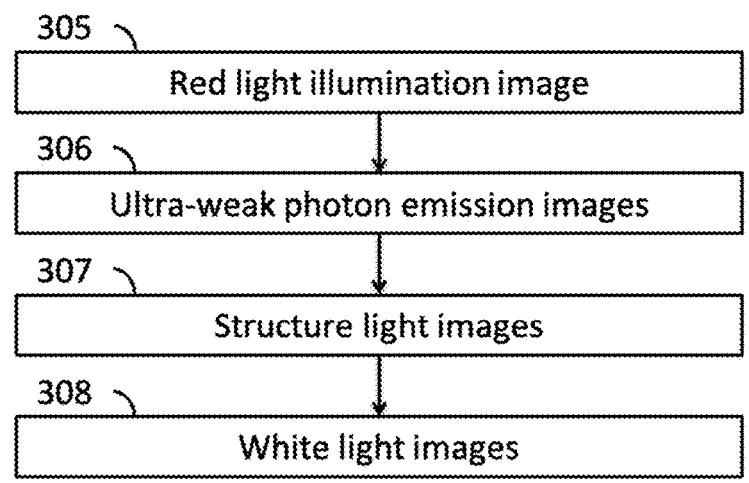

The sequence of image acquisition for physical integration multimodality embodiment is described in FIG. 3B, where an RL illumination Image is acquired first 305, a UPE image acquired second 306, SL images are acquired third 307, and a WL illumination image is acquired forth 308.

Specifically, in some embodiments, after applying LLLI to the target area, the method to capture the UPE image is first to have in the range of 1 second to 5 minutes, in the range of 30 seconds and 2 minutes, or as a non-limiting example nominally be set to 1 minute of safe RL illumination or light tight optical insulation. This time should be sufficient for relaxation of excited states in the skin and can also be used for rough optical alignment of the target area, optical insulation and fine alignment, as illustrated in FIG. 3A. Even with LLLI enhancement of the UPE, the intrinsic signal is ultra-weak and therefore a sufficiently long exposure is required for the UPE imaging. In some embodiments, the recommended total exposure time should be, in the range of 1 second to 60 minutes, in the range of 5 minutes to 45 minutes, or in the range of 10 minutes to 30 minutes, with a nominal time of 20 minutes. Acquisition time can be reduced or optimized to the desired or acceptable SNR, with the proper choice of the optical components.

In some embodiments, the optical detection tool, may be, but is not limited to, a charged couple device (CCD) camera that is ultra-sensitive, which means the CCD has high quantum efficiency (QE, i.e. the incident photon to converted electron ratio) in the visible to NIR spectral region, or nominally 400-1000 nm. In some embodiments, the long exposure imposes a constraint on the dark noise (dark current), which has a very strong temperature dependency. Therefore, the CCD may need to be cooled to a low enough temperature, as to enable proper function with high SNR and the long exposure time. The high QE requirement across the desired spectral range may be maintained at low operating temperature. Different designs of sensors can be used and in particular, but not limited to, the use of back-illuminated CCD, with deep depletion, and anti-reflectance coating is recommended. In some embodiments, the exposure time might be divided into shorter exposures, with proportionally more readouts and their associated noise.

In some embodiments, the use of electron multiplication CCD (EMCCD), intensified CCD (ICCD), complementary metal oxide semiconductor (CMOS), and comparable devices, may be applied. In these embodiments the dark noise suppression is inferior, which imposes much shorter exposure times limitation, and thus in these embodiments, a low readout noise is strongly recommended. A large sensor may enable the collection of more light, given constraints on the optics for the utilization of the entire sensor area. In some embodiments, different sensor technologies may be used, including but not limited to solid-state multi-pixel photodiodes array, avalanche diodes, multi-pixel photon counters (MPPC), silicon photomultipliers (SSPM, SiPM), or other. In some embodiments, the use of photodetector (photosensor) of any size and configuration, down to and including but not limited to a single photodetector, may be used to measure UPE.

In some embodiments, the LLLI and imaging may alternate to maximize the signal and/or SNR, and/or contrast, using different illumination and imaging duration and parameters. In some embodiments, the recommended total alternating duration should be, in the range of 1 second to 60 minutes, in the range of 5 minutes to 45 minutes, or in the range of 10 minutes to 30 minutes. As a non-limiting example, the alternating illumination and imaging sequence can be 5 minutes of illumination, followed by 5 cycles of 2 minutes imaging and 1 minute illumination for a total of 15 minutes, followed by 10 minutes imaging for a total sequence duration of 30 minutes.

In some embodiments, in order to correct for motion of the patient, and especially respiratory motion, different correction approaches may be applied. In some embodiments, movement monitoring of the patient is applied, using different technologies, including but not limited to passive and active infrared thermal imaging, mechanical sensor, acoustic and/or ultrasonic sensor, electromechanical sensor, laser sensor, and radiofrequency wave or microwave sensors. These technologies may provide gating or triggering data which enables synchronization of the imaging acquisition and the UPE imaging. In some embodiments, adaptive mechanical or optical tools may be used to compensate for the movement.

In some embodiments, the method further includes synchronization of the movement monitoring of the patient to the measured UPE imaging in order the compensate for the patient's movement using a free-breathing self-gated acquisition either during the measurement or by a post-acquisition correction. In some embodiments, because of the different trade-off of the detector's thermal noise and readout noise for movement monitoring and compensation, thereby taking many short exposure-time images increases the dominance of minimizing readout noise over thermal noise, different detector technologies, including but not limited to EMCCD, ICCD, CMOS, or other, should be used.

In some embodiments, the method further includes the use of immobilization of the target area, or part of the patient, or the entire patient, as demonstrated in FIG. 3A. Even with ergonomic and convenient accommodations for the patient, there is a risk that the patient will move during the exposure time. In such a case the UPE image would be smeared as an accumulation of the different positions of the target area as a function of time. While it is possible and recommended to ask the patient not to move, mechanical immobilization for the duration of the measurement should be strongly considered. The immobilization can be implemented is different ways, including but not limited to casts, splints, braces or collars, cushions, sheets, or other mechanical arrangement. In some embodiments, mechanical immobilization may include rigid and/or semirigid support for the optical detector and main imaging module to allow minimal movement while keeping continuously imaging stability.

In some embodiments, the method further includes optical insulation of the target area, as demonstrated in FIG. 3A. Optical insulation may reduce the amount of external and stray light detected by the imaging device. Because the UPE signal is ultra-weak, the sensor is ultra-sensitive and the exposure time is long, even a weak light leakage would affect the UPE measurement quality. The optical insulation may be achieved by the use of light absorbing or reflecting materials, also known as blackout materials. Metallic components, as well as organic and synthetic fabrics, flexible curtains, paper, rubber, cupboard, tape and other materials can be used as optical insulation materials. In some embodiments, the optical insulation also provides mechanical support for the optical detector of the main imaging module. In some embodiments, the optical insulation will focus on the of the target area, and will also cover, at least additional 5 cm or 2 inches, around the target area laterally to avoid light leakage through the skin and surrounding tissue to the target area. In some embodiments, the optical insulation will cover part of the patient, the entire patient, and/or may include optical insulation of part of, or all, the examination room.

In some embodiments, an exemplary method further includes an image-processing procedure for noise reduction and smoothing. The most common noise for UPE imaging is the so called "salt and pepper" noise, which can be mitigated by various approaches, including but not limited to smoothing and removing outlier data points. The smoothing procedure can be implemented in different ways, including but not limited to linear, median, Gaussian, and low pass filtering. Another way to smooth the image, which is not entirely software based, is binning of the sensors' pixels during the image acquisition. Binning of 2×2, or higher, at the expense of spatial resolution, can yield higher sensitivity and lower variability of signal. The optimal binning also depends on the target area and the size of the sensor used. In some embodiments, binning is used in the UPE image acquisition, including but not limited to 2×2, 4×4, 8×8, and 16×16.

In some embodiments, the exemplary method further includes image processing for boundary-based segmentation, contour finding, and edge detection. In some embodiments, the contour of the area of interest may be identified and marked manually, automatically, or a combination thereof. There may be different techniques to find edges, including but not limited to first order derivatives (e.g. Canny, Prewitt, Sobel) and second order approaches. As a pre-processing step to edge detection, a smoothing stage, typically Gaussian smoothing is commonly applied. The use of thresholds, with different threshold levels to find edges is also a common practice. The threshold levels can be determined manually, automatically or a combination thereof. These image processing procedures are illustrated in FIG. 5.

Figure 5A:
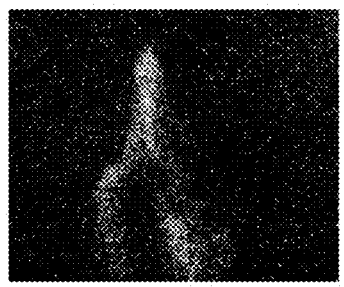
FIGS. 5A-F show an exemplary embodiment of a method of the present disclosure.
Figure 5B:
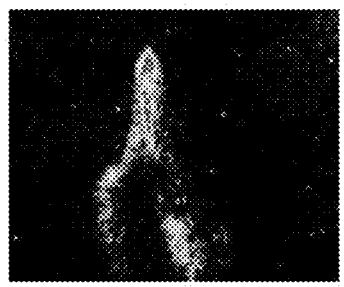
Figure 5C:
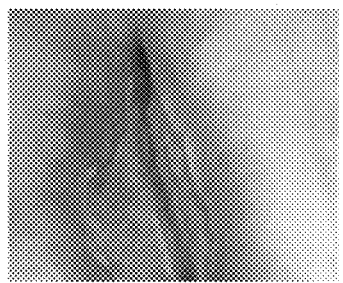
Figure 5D:
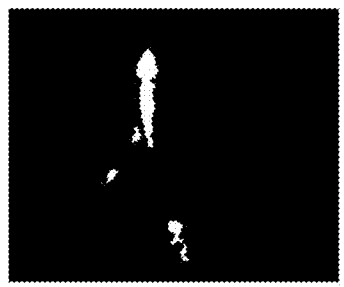
Figure 5E:
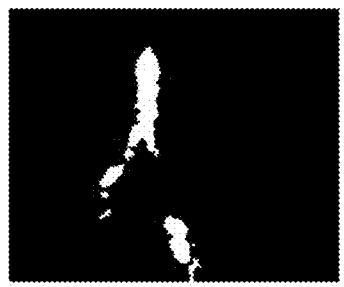
Figure 5F:
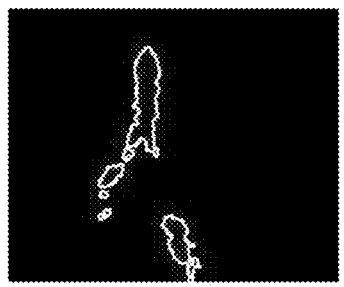

Specifically, FIGS. 5A-F provide an example for such analysis for a UPE image of the instant exemplary embodiments, starting with a raw image after noise reduction of outlier data points in FIG. 5A and smoothing procedure of this image to produce FIG. 5B. The colors represent intensity, using a jet color bar (blue to red). A WL illumination color processed image in 5C of a post-operative infection wound in the chest is presented as reference for the measured image. Two different levels of threshold applied to FIG. 5B are presented in FIG. 5D and FIG. 5E for high threshold and low threshold levels, respectively. Using the low threshold image of FIG. 5E, a contour analysis may be carried out to produce a contour image presented in FIG. 5F.

In some embodiments, the method further includes superimposing of two or more images or analyzed images. Each of the imaging modalities' image and analyzed image can be superimposed onto the other, where the superimposed image or analyzed images undergo additional processing to set its transparency level and in some embodiments choose a specific region to be displayed in the superimposed image without the rest of the image or analyzed image. When superimposing embodiments from two different measurements, the superimposing procedure requires the identification and marking of reference points, which can be done automatically, manually or a combination thereof. The reference points are then used to match different images and analyzed images onto another, with corrections of spatial orientation, size and other parameters. In some embodiments of the present exemplary embodiments, different optical imaging modalities can be integrated into one imaging device, which allows for seamless co-registration of images and analyzed images. In these embodiments, images and analyzed images of the different imaging modalities can be superimposed with high accuracy, without the need for reference points and additional correction procedures.

Exemplary embodiments of the present disclosure may further include a physical integration of a UPE imaging module with other imaging modalities modules into one imaging device, with the main detector being the instant exemplary embodiments' detector, i.e. the detector used to capture UPE images with and/or without filters. In some embodiments, the other imaging modalities, with all their respectively associated modules of illumination sources and filters may also include, but not limited to, RL imaging, WL imaging, and SL imaging, as illustrated in FIG. 6 (discussed in detail below).

In some embodiments, these additional components may be integrated in different geometries to achieve high-quality imaging. There are at least two advantages to such integration. First, instead of having two, three or more imaging devices, only one multi-modality device is required. Second, by using one imaging device, with the same optical settings, a seamless co-registration of all the imaging modalities is achieved. The same target area can be imaged, using different imaging modalities, without the need for reference points and complex analysis which is required when working with images and analyzed images from different devices. In some embodiments, the immobilization of the target area, or at least the area of interest, may become a pre-requisite in the application of a serial imaging scheme, as demonstrated in the method FIG. 3A.

In some embodiments, the integrated device will use RL illumination source that does not optically excite the patient's body, and particularly the skin, including but not limited to a dark red LED or a filter that removes the higher-energy shorter wavelengths (edge filter, band pass filter, or other).

In some embodiments, the method includes the physical integration of RL and WL imaging, including but not limited to LEDs arranged in a variety of geometries. In some embodiments, the WL can be composed of a combination of blue light, green or yellow light, and red light. The combination of blue, green, and red lights can be used to reconstruct a natural color processed image, where the processing is only the combination of the red, green and blue (RGB) images with the right color balance. In some embodiments, the WL illumination can be white illumination sources (broad visible spectrum), including but not limited to LEDs. In some embodiments, the integrated device will include additional filters in the visible range for the WL illumination, including but not limited to red, green and blue filters, to enable natural color processed image, where the processing is only the combination of the filtered images with the right color balance.

In some embodiments, the method further includes the physical integration of SL imaging, where the SL is detected by the imaging system, with or without the use of one or more filters to produce an accurate surface reconstruction map of the target area or any region therein. The problem SL is trying to solve is that the measured surface is not flat, but curved. Therefore, assessment of the area of interest area in particular is likely inaccurate and skewed. SL is a noncontact technique that usually uses projected laser beams, with different patterns (dots, lines, or other) that distort with the curvature, depth, and irregularity of a measured surface. The mechanism creates a topographical model of the target area using at least two captured images with different positions of the laser beams. The implementation is not limited to laser beam but can apply to any comparable light source. The light source may comprise of an LED array, liquid crystal display (LCD), lasers, laser diodes and/or filtered lights, and/or polarizers, or other components arranged in a variety of geometries. The imaging is recorded on the imaging device after passing through no filter, or one or more different filters and/or polarizers in the visible and NIR spectral ranges sequentially to obtain at least one or two images to be analyzed. The processing of the structured light images may produce a surface reconstruction map, which maps the curvature of the measured target area to a 3D representation model, which corrects the area of the target area, and the area of interest in particular. In some embodiments, a similar analysis of curvature assessment and boundary detection can be implemented by illuminating light directionally instead of uniformly, which means to illuminate RL and/or WL illumination, or other. Non-limiting examples of 3D mapping are also disclosed in "Structured-light 3D surface imaging: a tutorial", by Jason Geng, published in Advances in Optics and Photonics 3, 128-160 (2011), which is herein incorporated by the reference in its entirety.

In some embodiments, a reconstruction map from SL images or equivalent mapping technique is incorporated in the analysis. The reconstruction map can be used to reconstruct all other images and analyzed images, measured using other modalities to correct for the curvature of the area of interest and/or target area. Both the original images and the corrected images can be saved and be accessible to the users. The process of this procedure is to obtain the correct measures of the pathological condition size, shape and other spatial characteristics. Correct spatial measurements may also provide a more reliable base for longitudinal monitoring of the pathological condition.

In some embodiments, a signal reconstruction algorithm may be applied to retrieve the optical-spatial information of deep tissue signals. The light emitted by a hot spot deep inside the body will scatter and some of it will end up emanating from the skin. In some embodiments, primarily where the pathological condition is in the skin, or subcutaneously close to the skin, the UPE image will represent well the underlying pathology with minimal additional reconstruction analysis. In some embodiments, primarily deeper into body in relatively isotropic tissues, the signal reconstruction algorithm will be based on the radiative transfer equation, including but not limited to the diffusion approximation, similar to fluorescence molecular tomography and bioluminescence tomography. In some embodiments, such as those instances of the deepest applications with least isotropic tissues, the signal reconstruction algorithm may be based on autocorrelation reconstruction. In some embodiments, a signal reconstruction algorithm may be based on a combination of signal reconstruction algorithms mentioned, or on a different reconstruction algorithm.

In some embodiments, the signal reconstruction algorithm may use the 3D mapping of the UPE signal, resulting from the surface reconstruction algorithm, and incorporate it in the analysis. In some embodiments, the signal reconstruction algorithm may use UPE signal collected from one, two, or more detectors, at different angles, to improve the reconstruction and allow for higher precision of the optical-spatial information.

In some embodiments, NIR multispectral imaging (MSI) may be incorporated in the analysis. The purpose of the NIR MSI is to assess quantitatively the blood flow and perfusion, and oxidation of the tissue. These tissue properties provide an important assessment of the viability and wellbeing of the measured tissue, as they relate to the supply of oxygen and other nutrients into the tissue, as well as the removal of waste product out of the tissue. Poor perfusion and lower oxidation harm the tissue and inhibit recovery. The MSI image can be further analyzed to remove noise, correct background, apply a smoothing algorithm, identify contours, identify hot spots by defined thresholds, or undergo other image processing procedure. By superimposing on, and comparing and contrasting the NIR MSI images, analyzed images and the oxidation and perfusion images with UPE imaging, a more detailed clinical profile may emerge. The combination of these modalities may enable identification of areas which suffer from hypoxic conditions and differentiating these areas from other area which suffer from bacterial infection and/or inflammation without exhibiting hypoxic conditions, i.e., areas, which exhibit high UPE signal, but normal oxidation and perfusion levels.

For example, a non-limiting embodiment is early-stage pressure injuries, in which a temporary pressure or shear reduced the blood flow and caused damage to the tissue, but upon release the flow of blood is restored. The tissue will exhibit oxidative stress and inflammatory response, which would be detected by UPE imaging, but limited indication will be manifested in the oxidation and perfusion images calculated from the NIR MSI. On the other hand, in a venous stasis ulcer, one expects to see an overlap of the signals form UPE imaging and NIR MSI in the hypoxic areas of the wound. The analysis is objective and quantitative, thus requiring limited additional interpretation.

In some embodiments, NIR MSI may also be physically integrated to the UPE imaging platform, and on the imaging device module specifically, to allow for seamless co-registration. A non-limiting embodiment of NIR MSI integration is illustrated in FIG. 6B and FIG. 6C.

In some embodiments, autofluorescence (AF) imaging may be incorporated in the analysis. The purpose of the AF imaging is to assess the existence, location and severity of a bacterial infection and provide a bacterial load image. The bacterial load image can be further analyzed to remove noise, correct background, apply a smoothing algorithm, identify contours, and identify hot spots by defined thresholds, or undergo other image processing procedure. By superimposing on, and comparing and contrasting the AF images, analyzed images and the bacterial load image with UPE imaging, a more detailed clinical profile may emerge. The combination of these modalities enables the identifications of areas, which suffer from bacterial infection and differentiating these areas from other areas, which suffer from hypoxic conditions and/or inflammation without bacterial infection. For example, a non-limiting embodiment in which the bacterial infection causes hypoxic conditions or inflammation, and the UPE imaging helps identify the most active hot spot to be treated with most care using local debridement or application of local antibiotics. In other non-limiting embodiments, the patient may be exhibiting more than one issue. For example, one part of a wound may suffer from bacterial infection while another part may suffer from hypoxic conditions. Such clinical insight would produce more accurate treatment plan, which may help a faster healing process. The analysis is objective and quantitative, thus requiring limited additional interpretation.

In some embodiments, AF imaging may also be physically integrated to the UPE imaging platform, and on the imaging device module specifically, to allow for seamless co-registration.

In some embodiments, thermography or thermal imaging is incorporated in the analysis. The purpose of the thermal imaging is to assess the changes in temperature of the superficial tissue. Changes in temperature are associated with pathological conditions. For example, inflammation would usually exhibit higher temperature compared to healthy tissue and hypoxic conditions in the tissue would exhibit lower temperature compared to an adjacent healthy tissue. The thermal image, acquired using active or passive thermal imaging device, can be further analyzed to remove noise, correct background, apply a smoothing algorithm, identify contours, and identify hot spots by defined thresholds. By superimposing on, and comparing and contrasting the thermal images, analyzed images and the thermogram (temperature image) with UPE imaging, a more detailed clinical profile may emerge. The combination of these modalities enables the better identifications of areas, which suffer for example from inflammation (high temperature and high UPE signal) or hypoxia (low temperature and high UPE signal). The analysis is objective and quantitative, thus requiring limited additional interpretation.

The present exemplary embodiments may further include methods to incorporate in the analysis other imaging modalities' images and analyzed images, including but not limited to, CT and MRI. Incorporating in the analysis other imaging modalities' images and analyzed images may provide better visualization, and synergetic differential analysis abilities, which help detect, diagnose, prognose, as well as recommend, support, guide and assess treatment more effectively. Incorporation of CT or MRI images in the analysis may aid in the determination of the size, shape and other spatial characteristics of the pathological condition. By combining the structural (CT, MRI) imaging modalities to the analysis of the UPE imaging, a clinician may be able to obtain a comprehensive visualization and characterization of the pathological condition. The synergetic diagnostic utility of such analysis would help to provide the most personalized and informed treatment to patients. By applying this approach longitudinally, the progression of treatment may be monitored and adjusted for optimal outcome.

UPE imaging may be viewed as a molecular imaging modality, similar in some ways to positron emission tomography (PET). In some embodiments, UPE images can be superimposed on CT or MRI images, in a similar way PET images are superimposed on CT or MRI images. In some embodiments, a multimodality machine can be implemented, similarly to PET/CT and PET/MR, the multimodality machine may be LLLI-UPE/CT and LLLI-UPE/MR. While the potential synergy of such integration might be useful, the advantage of the LLLI-UPE device in terms of cost and measurement without the use chemicals or ionizing radiation, will be diminished.

In some embodiments, the method further includes a medical record system, which records all the acquired images, analyzed images, regions, superimposed images, compare and contrast images for all recorded measurements, for each patient, in a secured way. The medical records are kept in compliance with HIPAA guidelines and regulations.

In some embodiments, the method may further include using one or more personalized decision support algorithms based on the data collected from all the measurements, for a specific condition, stage and the progression (healing/deterioration) of the pathological condition as a function of time. In some embodiments, the medical images can be analyzed by various statistical tools and advanced analysis, including but not limited to, machine learning algorithms, deep learning algorithms, neural networks algorithms, artificial intelligence algorithms, or other.

Figure 4:
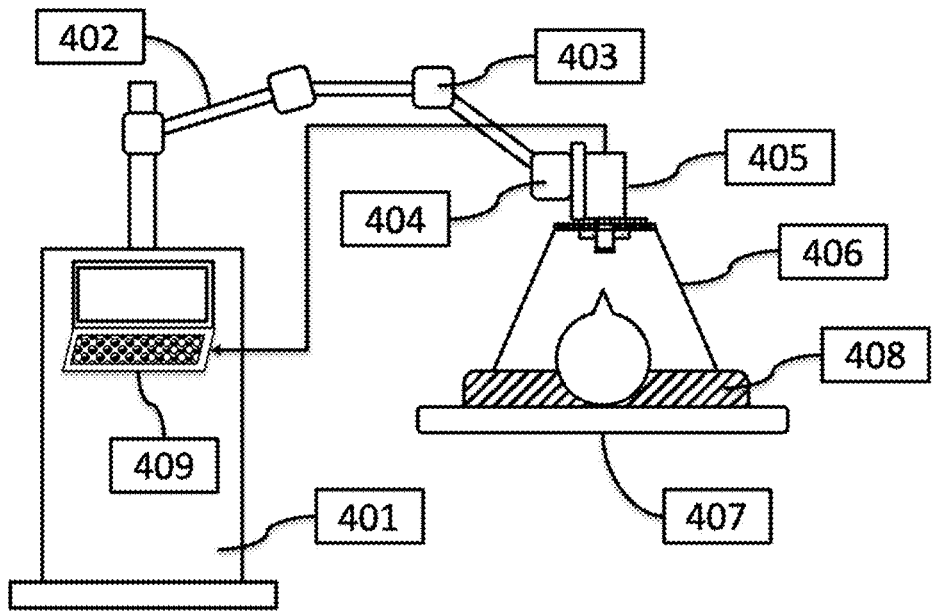
FIG. 4 is an illustration of the UPE imaging system according to an exemplary embodiment of the present disclosure, including system components and data flow.

An exemplary embodiment of the physical system for executing the UPE imaging methods disclosed herein is illustrated in FIG. 4. As shown in FIG. 4, the system may include a unit 401 that may be configured to carry all of the mechanical, electrical, and optical components, including the computer. In some embodiments, the unit 401 may be a cart. The unit 401 may be stationary or may be configured to move.

FIG. 4 further depicts that the system includes a mechanical arm 402 that is connected to the unit 401. The mechanical arm 402 may include flexible joints 403 and a connector 404. In some embodiments, the connector 404 has more degrees of freedom of movement than the flexible joint 403. As shown in FIG. 4, an imaging module 405 may be connected to the connector 404. The mechanical arm 402 may be configured to move so that the imaging module 405 may be positioned in an optimal location and orientation with respect to the patient 408.

Figure 6A:
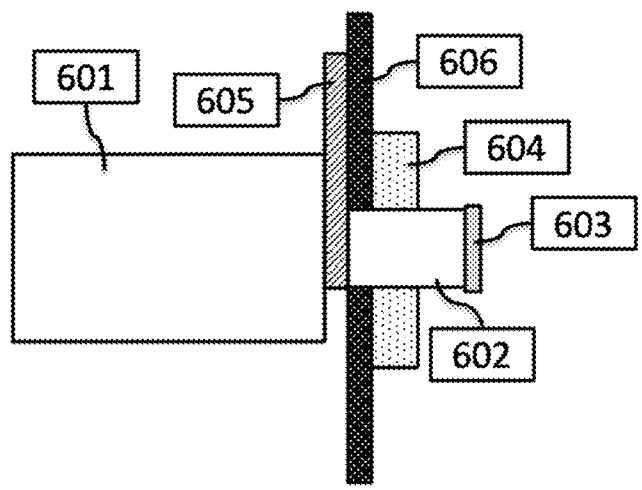
FIGS. 6A-6C depict imaging components of an exemplary embodiment of the present disclosure.
Figure 6B:
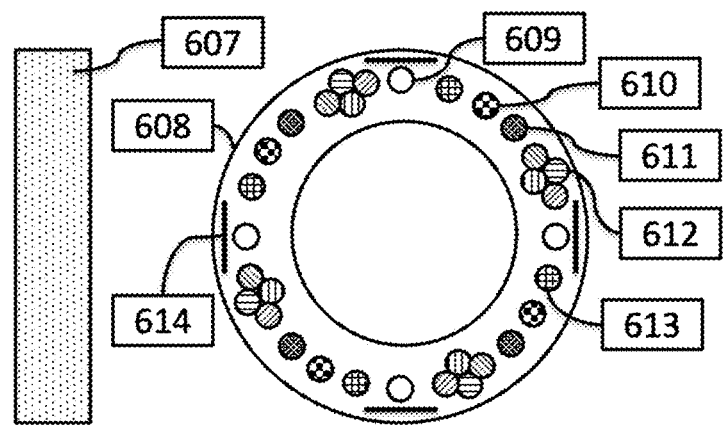
Figure 6C:
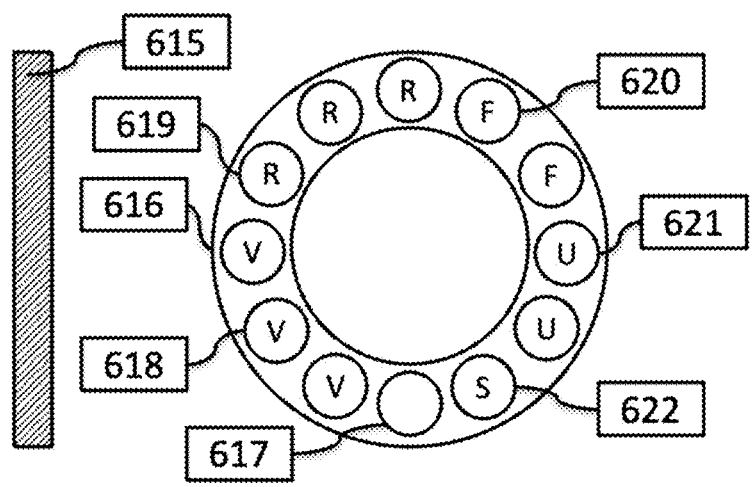

FIGS. 6A-6C depict exemplary embodiments of the imaging module 405. For example, as shown in FIG. 6A, the imaging module may include an imaging component 601, which may be a high sensitivity sensor or camera. In some embodiments, an optical insulation unit 606 may be attached to the imaging component 601, to ensure optimal optical insulation. In some embodiments, the optical insulation unit 606 may be part rigid and/or part semirigid, and/or part flexible to ensure that the handling of the imaging module is convenient.

The imaging component 601 may further be connected to a lens 602, which has a lens cover 603. In order to achieve proper imaging on the imaging component 601, the lens 602 may be placed between the patient 408 and the imaging component 601. There are a few considerations for the choice of lens, including (1) the materials of the lens, including the coating, have to be with low absorption in the desired spectral range (400-1000 nm); (2) a compound lens, i.e. a lens system consisting of two or more lenses on the same axis, will enable full or partial correction of different aberrations, such as chromic aberration. On the other hand, more optical components means more reflection losses and more absorption of the incident signal; (3) a larger diameter of the lens system and aperture allows for more light to go in and increase the signal, at the cost of being cumbersome, and extending the focal length and working distance of the lens; and (4) the working distance of the lens sets the solid angle of target area and given the ratio of the working distance and the aperture diameter (also known as f-number)—the numerical aperture. Therefore, there is a trade-off between how large the target area is and how much light can be collected efficiently.

Another consideration for choosing a lens is whether it is a fixed lens or an adjustable lens. One advantage of a fixed lens is that once focus is achieved on the entire or at least most of the target area, the working distance is known and thus the dimensions on the target area are known. In some embodiments, mechanical support can assist in setting a reproducible and stable working distance. On the other hand, an adjustable lens may be easier to use and may require less alignment time. The use of an adjustable less requires either a way to know exactly the magnification of the lens (a function that exists in some models of adjustable lenses) or a way to calibrate the distances on the target area, such as marking of known distance (marked using a ruler).

In some embodiments, the lens may be a mirror lens, which may minimize chromatic aberration and has its own tradeoffs. In some embodiments different types of lenses can be used, including but not limited to single or compound lens, fixed or adjustable lens, refractive or mirror lens. In some embodiments, alternative imaging solutions may be implemented, including but not limited to, lensless imaging, holographic imaging, polarization imaging, optical fiber, optical fiber bundle, non-imaging optics including but not limited to concentrators, a combination thereof, or other.

The imaging module 405 may further include an illumination unit 604, for multimodality physical integration embodiments. In some embodiments, the illumination unit 604 may be connected just after the lens and may incudes illumination components for the different modalities, which is depicted in FIG. 6B.

FIG. 6B depicts a side view 607 and a front view 608 of the illumination unit 604. In addition, FIG. 6B depicts an exemplary embodiment of a configuration for the number, type and spectral range of the illumination components for the different modalities. For example, the illumination unit 604 includes WL 609, RL 610, green light 611, NIR MSI light sources for 612, blue light for AF excitations and balanced RGB color imaging 613, lasers or other structured light for alignment and SL mapping 614. The arrangement, number, type, and spectral range of SL may vary based on the embodiment. The illumination unit power may be connected to the computer for control 409 and to an electric power supply (not shown). In some embodiments, the illumination module may include LLLI, making the enhancement and imaging integrated into a single module.

FIG. 6C depicts an exemplary embodiment of a filter wheel 605, which may be configured to complement the illumination unit 604 of the imaging module 405. In FIG. 6C, a side view 615 and a front view 616 of the illumination unit are presented. The filter wheel 605 may include one slot without a filter 617, three filters in the visible range denoted as "V" 618, three NIR MSI in the NIR range denoted as "R" 619, two AF imaging filters in the visible and/or NIR range denoted as "F" 620, two UPE imaging filters in the visible and/or NIR range denoted as "U" 621, and one filter in the visible and/or NIR range for structured light denoted as "S" 622. The arrangement, number, type, and spectral range of filters may vary based on the embodiment.

In some embodiments, the UPE spectral characteristics can be further analyzed by the use of filters depicted in FIG. 6C. For example, by analyzing the spectral characteristics of the UPE image, valuable medical information can be retrieved, such as a differential diagnostic, as different pathological conditions have different spectral pattern (e.g. inflammation vs. cancer tumor vs. infection). In some embodiments, the filters can be used to create filtered images with spatial information. In other embodiments, the filters can be used to provide more detailed spectroscopic data at the expanse of the imaging, including but not limited to diffractive optical components. In some embodiment, different types of filters can be used, including but not limited to short or low pass, high or long pass, band pass, band stop, and any combination thereof. In some embodiment, different filter technologies can be used, including but not limited to, different materials, coatings, use of liquid crystal tunable filters (LCTF), acousto-optic tunable filters (AOTF), linear variable filters, or other. In some embodiments, a series of UPE images are taken through different filters or no filter. The filtered UPE image or images are then processed and analyzed using the relevant image processing tools and procedures.

In some embodiments, the UPE signal is analyzed using a spectrometer with or without spatial filtering, to better and more completely retrieve information from the spectral characterization of the signal.

Returning to the system depicted in FIG. 4, optical insulation 406, including for example, blackout materials, may additionally be included in the system, which as discussed herein, may be configured to insulate the imaging module, the patient 408, and/or the patient's target area designated to imaging.

In the exemplary embodiment of FIG. 4, a computer 409 may be positioned on the unit 401 and may be optically insulated. However, in other embodiments, the computer 409 may be positioned outside the exam room due to the light emitted from the screen.

In some embodiments, the system of FIG. 4 may be positioned in an optically insulated, enclosed space inside the examination room. In other embodiments, the optical insulation will be confined to the surrounding of the target area, nominally 5 cm or 2 inches around the target area to avoid light leakage through the skin. Optical blackout material can be used to insulate from external and stray light.

Figure 7:
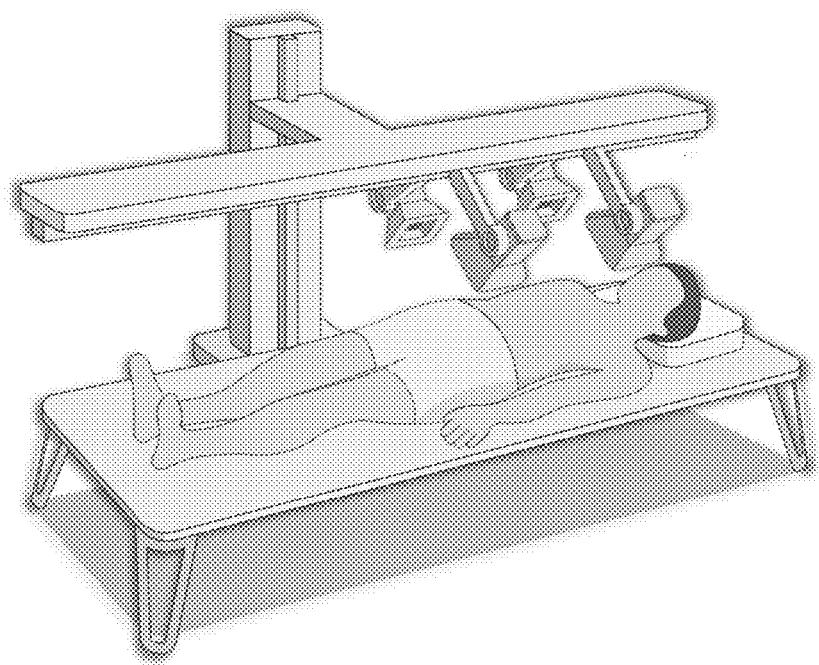
FIG. 7 is a 3D illustration of UPE imaging system according to an exemplary embodiment of the present disclosure, with four imaging devices and an adjustable mechanical apparatus.

The system of FIG. 4 includes a single imaging module 405. However, in some embodiments, the system may include multiple imaging modules. For example, the system depicted in FIG. 7 includes multiple imaging modules measuring multiple target areas, with different orientations, mounted on an adjustable mechanical support. In some embodiments, the one or more imaging modules 405 may be positioned at different orientations with respect to the patient, as illustrated in FIG. 7.

Figure 8:
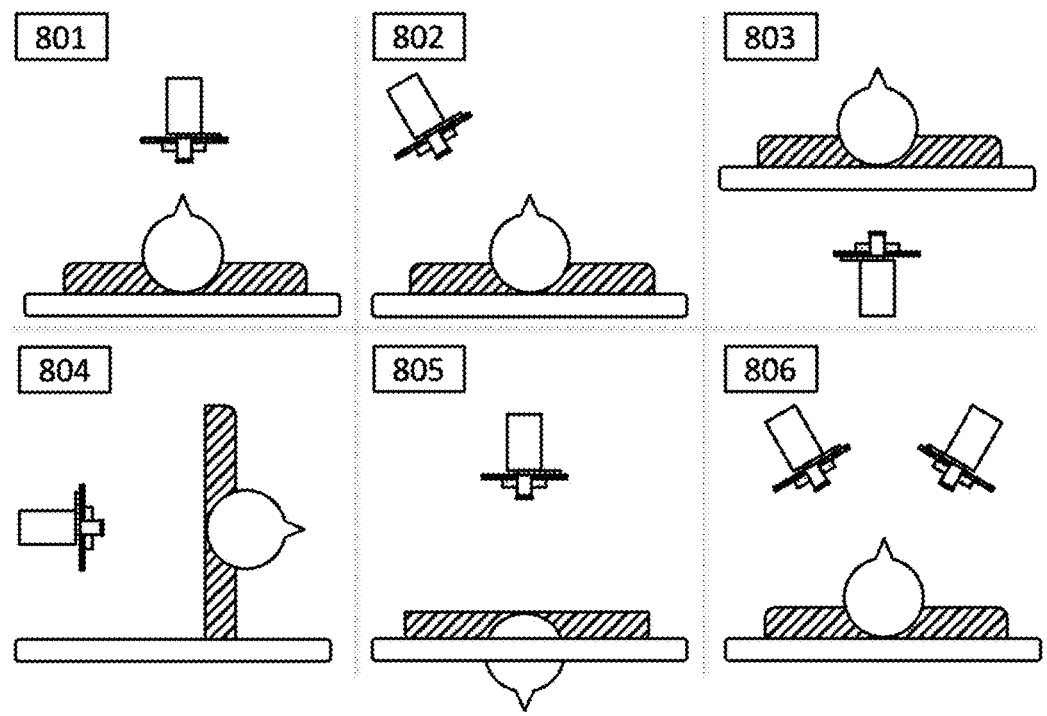
FIG. 8 is an illustration of different orientations of an exemplary UPE imaging system.

Specifically, FIG. 8 depicts that measurements can be performed in various orientations of the imaging module and of the patient. These orientations include, but not limited to, imaging straight down a patient lying supine 801, imaging in an angle a patient lying supine 802, imaging straight up a patient lying supine 803, imaging from the side a patient lying sideways 804, imaging straight down a patient lying prone 805, and imaging a patient lying supine from multiple orientation using more than one imaging device 806. The optimal orientation would depend on the patient's condition and the pathological condition being measured.

In some embodiments of the present disclosure, including the system of FIG. 4, may be configured to perform one or more of the following functions, including, optical signal detection, signal input into a processing unit, and display capabilities, where the functions can be installed, e.g. in a dedicated procedure room or at the point of care. In some embodiments, the present exemplary embodiments are at least one module and are integrated into or merged with another existing or future equipment to create a new device.

Clinical use of the exemplary systems and methods of the present disclosure will now be discussed. There are currently no techniques or procedures for measuring optically, without the use chemicals (biomarkers, contrast agents, labeling compounds, radiotracers, etc.) or ionizing radiation, non-invasively and locally oxidative stress in the clinical setting. While biomarkers in the blood are used to assess the holistic oxidative stress level, local detection of oxidative stress non-invasively is not available. In many pathologic conditions, oxidative stress is deeply correlated to the pathological condition, and acts as either the cause and/or the consequence. Many times, feedback mechanism increase the manifestation of oxidative stress (for example, infection and the inflammatory response to the infection). The following, non-limiting examples, are presented as illustrations for the broad utility of the instant exemplary embodiments.

Exemplary embodiments of the present disclosure focus on skin and soft tissue pathological conditions, including but not limited to chronic wounds such as a diabetic (foot) ulcer, venous stasis ulcer, pressure ulcer, burn, vasculitic (leg) ulcer, and post-operative infection, at any stage; a chronic wound; a malignant wound, such as a primary cancer or a metastasis to the skin from a local tumor or from a tumor in a distant site; a skin cancer, including but not limited to melanoma, basal cell carcinoma, squamous cell carcinoma or other; a cancer metastasis in the skin and/or subcutaneously; an acute wound such as traumatic wounds or surgical wounds, including but not limited to plastic surgery; and skin and soft tissue infections from bacterial, fungal, viral, or parasitic sources. Chronic wounds are in their essence vascular problems, which manifest oxidative stress in at least three ways: hypoxic conditions of the tissue as a result of poor perfusion of blood and low oxidation of the tissue, infection from external bacteria and build-up of bacterial load, and inflammation as part of the healing process, and as a response to, but not limited to, a bacterial infection. Other skin wounds and other pathological conditions exhibit similar manifestations of oxidative stress.

In some embodiments, such as pathologic conditions involving the skin and soft tissues, it is possible to image the skin and provide quantifiable and objective measure of oxidative stress, which is associated with the pathology. The measure of the oxidative stress can be used to differentially diagnose, prognose, recommend, support, and guide treatment regimen, and assess treatment efficacy.

In some embodiments, UPE imaging of pathological conditions involving the skin and soft tissues can allow for the identification of hot spots, areas with high intensity signal, which are associated with high oxidative stress. The identification of the hot spots can allow for better analysis and prognosis to recommend and guide better treatment regimen. For example, if the hot spot is a result of an infection, identifying the hot spot can provide a significantly better sampling of a bacterial infection by swabbing or biopsy, as well as follow-up measurements of the infected area.

Figure 9A:
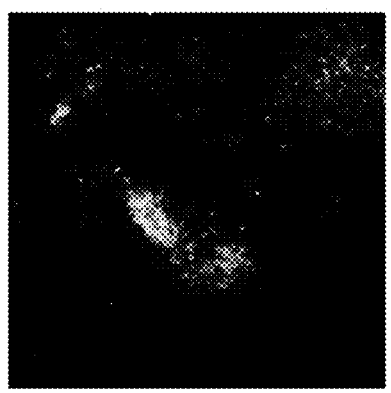
FIGS. 9A-C show an exemplary embodiment of the present disclosure used for the detection of a diabetic foot ulcer.
Figure 9B:
Figure 9C:

FIGS. 9A-C depict an exemplary embodiment of the present disclosure using UPE imaging for the monitoring of a diabetic foot ulcer. FIG. 9A is an UPE image, which shows an infection hot spot in the wound. FIG. 9B is a RL illumination image. FIG. 9C is a superposition of the UPE image (FIG. 9A) and a RL illumination image (FIG. 9B). In some embodiment, the superposition, illustrated in FIG. 9C, may provide better visualization, and allows and the user to easily identify the UPE active regions in the area of interest of the target area.

In some embodiments, UPE imaging can be used for screening of different pathological conditions to allow the application of preventive treatment. The pathological conditions may include, but are not limited to, venous stasis, arterial insufficiency, prolonged unrelieved pressure/sheer which can be continuous or intermitted, ischemic-reperfusion injury, and diabetes and other vascular problems, which can result in ulceration. UPE imaging can find the hot spots of the hypoxic and/or inflamed tissues, and direct clinical care to those areas. By focusing the treatment to a specific location, ulceration or at least infection of these sites may be avoided. Targeted screening and treatment may reduce the likelihood of complications and enable faster healing.

In some embodiments, UPE imaging may allow for the efficacy of administered drugs, or other treatments, to be directly observed and/or quantified, and may further allow for better guidance for treatment, such as continuing with the current treatment, changing the dosage or other elements of the treatment, changing the type of treatment, etc. In some embodiments, UPE imaging may allow for longitudinal assessment of the tissue, with the progression of the disease. In some embodiments, continuous monitoring of the same patient can be used to help assess the efficacy of treatment and help recommend, support and guide treatment regimen. By comparing and contrasting UPE images at progressive treatment sessions, the spread of the oxidative stress spatially and its overall intensity, in combination with other physiological parameters and indicators and their progression, can be assessed.

FIGS. 10A-C depict an exemplary embodiment of the present disclosure using UPE imaging for the monitoring of a venous stasis ulcer in the leg. FIG. 10A is an UPE image, which shows hypoxic conditions hot spots in the wound. FIG. 10B is a WL illumination color processed image. FIG. 10C is a superposition of the UPE image (FIG. 10A) and the WL illumination color image (FIG. 10B). The superposition illustrated in FIG. 10C, provides better visualization, and allows the user to easily identify the UPE active regions in the area of interest of the target area.

In some embodiments, by comparing and contrasting UPE images at progressive treatment sessions, the spread of the wound and its overall intensity, as well as other pathological conditions and their progression, can be assessed.

In some embodiments, UPE signal is an indication of the underlying pathological condition of the chronic wound and can be used to recommend treatment regimen. The treatment regimen in the case of infection might include drug treatment, including, but not limited to, topical antibacterial such as metronidazole, mupirocin, tulle, silver containing ointments, anti-matrix metalloproteinases, acetic acid, hyaluronic acid, and povidone iodine, or other. Other wound care treatment procedures may include, but not limited to, regenerative stem cells therapy, enzymes such as collagenase, papain, fibrinolysism, or other, and growth factors such as platelet-derived growth factor, epidermal growth factor, or other. The wound care treatment regimen can also include different dressings, including, but not limited to, hydrogels, hydrocolloids, alginates, foam, silver impregnated dressings, artificial skin, non-adherent dressing, wet to dry dressing, silicon impregnated atraumatic dressings, transparent film dressings, vacuum aided devices, negative pressure dressings, or other. In some embodiments, there would be a correlation of the measured amount of UPE signal in the area of interest of the target area to the at least one recommended treatment regimen for the chronic wound.

In some embodiments, UPE can assess the effectiveness of different treatments to improve the condition of chronic wounds, for example hyperbaric oxygen treatment (HBOT), and other pathological conditions. HBOT is used to reduce inflammation and hypoxic conditions in the chronic wound, and help the body fight infections, by exposing the body to high concentration of oxygen, up to pure (100%) oxygen, under high-pressure (hyperbaric) conditions. HBOT enables the body to carry more oxygen to the chronic wound, which the wound needs to heal faster and fight infection. The effectiveness of the treatment has large variability. In order to allow personalized assessment for the effectiveness of treatment, UPE imaging can measure the wound longitudinal. A baseline measurement is taken before the first HBOT session and compared and contrasted to subsequent sessions. The size of the wounds, as well as the intensity and area of the strong UPE signal, is used to assess the effectiveness of the treatment. A reduction in the UPE signal would mean an improvement in the hypoxic conditions, and/or the inflammation, and/or the infection, which can be used as indicators for the success of the treatment and encourage continuation of the HBOT regime. If the UPE imaging shows that there is no change or if there is a deterioration of the wound, then the HBOT treatment has to be modified and/or alternative treatment should be considered. The treatment feedback can be achieved within a minimal number of HBOT sessions, allowing faster healing with better allocation of treatment resources. HBOT treatment may be used in other pathological conditions, for which UPE imaging can be used to assess the treatment effectiveness, including but not limited to traumatic brain injury, infection in a bone (osteomyelitis), chronic infection (actinomycosis), delayed radiation injury, or other. In some embodiments, different treatments with variable effectiveness, which can be analyzed using similar assessment procedure, include, but not limited to, photodynamic treatment, low-level light therapy, ultrasounds therapy, or other. In some embodiments, UPE signal is an indication of the underlying pathological condition of the chronic wounds and can be used to recommend treatment regimen which includes, but not limited to, hyperbaric oxygen treatment, photodynamic treatment, low-level light therapy, or other.

In some embodiments, UPE imaging can provide assessment for the wellbeing of the tissue by differentiating between healthy, stressed, and necrotic tissues, which can be used for monitoring as well and providing surgical margins assessment to recommend appropriate treatment regimen. As a non-limiting example, in pathological conditions such as diabetic foot ulcers, the progression of the disease leads to deterioration of the vascular support of the foot. The tissue becomes hypoxic, with a complex inflammatory response. In case of ulceration, the body also struggles to fight infection. When the tissue deteriorates further, gangrene develops, and amputation becomes necessary. UPE imaging allows for longitudinal assessment of the tissue, with the progression of the disease. When the tissue becomes unsalvageable, UPE imaging can help identify the viable tissue boundaries to allow for minimal partial amputation. UPE imaging will show the necrotic tissue as dark and the adjacent living inflamed and hypoxic tissue as bright, while the healthy tissue will have a weak consistent signal. In some embodiments, including but not limited to skin cancer, UPE imaging can be used to provide surgical margins of the pathological condition, including, for example, in a Mohs micrographic surgery. Thus, objective, quantifiable UPE image can assist with determining the exact area and the timing of the recommended surgical procedure. This information can reduce the trauma for the patient, expedite recovery from the surgery, and reduce the likelihood of a subsequent surgery. In some embodiments, UPE signal is an indication of the underlying pathological condition of the chronic wounds and can be used to recommend treatment regimen which includes, but not limited to, Mohs micrographic surgery, partial amputation, corrective surgery, plastic surgery, vascular surgery, or other.

In some embodiments, UPE can also assist in guiding debridement, which involves the removal of dead, damaged, or infected tissue, which improves and promotes the healing potential of the remaining healthy tissues. This common treatment procedure in wound care requires differentiating between healthy, stressed and necrotic tissues. Along with cleaning, brushing and suction, the process of debridement, includes, but limited to, surgical or sharp, autolytic, mechanical, chemical or enzymatic, maggot-based debridement, or other. The proper application of targeted and effective debridement, as well as assessment of the efficacy of the procedure, can be achieved by the UPE imaging ability to provide information regarding the wellbeing of the tissue at different locations with suitable spatial resolution. In some embodiments, UPE signal is an indication of the underlying pathological condition of the chronic wounds and can be used to recommend debridement treatment regimen which includes, but not limited to, surgical or sharp, autolytic, mechanical, chemical, or enzymatic, maggot-based debridement, or other.

In some embodiments, after a surgery, UPE imaging can provide longitudinal measurements assessing the viability and wellbeing of recovering tissues. As a non-limiting example, such tracking can be used to determine whether or not a surgical wound is healing properly with good vascularization and the right level of inflammation, as well as to verify the absence of post-operative infection, dehiscence of skin grafts and skin flaps, and other complications which can harm the tissue, inhibit the recovery and prolong the healing process.

In some embodiments, the instant exemplary embodiments focus on cancer, primarily solid tumors, including but not limited to, bladder cancer, brain cancer, breast cancer, cervical cancer, colon and rectal endometrial cancer, kidney cancer, lip and oral cancer, liver cancer, lung (small cells and non-small cells) cancer, melanoma and nonmelanoma skin cancer, mesothelioma, oral cancer, ovarian cancer, pancreatic cancer, prostate cancer, sarcoma, thyroid cancer, or other. Chronic inflammation and oxidative stress are directly related to carcinogenesis. Oxidative stress is also manifested in angiogenesis and chronic hypoxic conditions in the tumor microenvironment, as well as inflammatory response to the tumor. The analysis includes both the primary tumor and metastases, in any part of the body. In some embodiments, the exemplary embodiments include measuring all stages of cancer development, including before, during and after any treatment. In some embodiments, UPE signal is an indication of the underlying pathological condition of the cancer and can be used to recommend treatment regimen including but not limited to surgery, including but not limited to biopsy, staging, debulking, tumor removal, also called curative or primary surgery, medication including but not limited to chemotherapy, immunotherapy, hormone therapy, targeted drug therapy, radiopharmaceuticals, photodynamic therapy, or other, radiation therapy including but not limited to external beam radiation therapy, internal radiation therapy, or other, any type of ablation, including but not limited to cryoablation, thermal ablation, optical ablation, radiofrequency ablation, thermo-mechanical ablation, focused ultrasound ablation, or other. Application of treatment is likely to have an effect on the surrounding tissue oxidative stress level, which are likely to affect the UPE measurement. In some embodiments, there would be a correlation of the measured amount of UPE signal in the area of interest of the target area to the at least one recommended treatment regimen for the cancer.

FIG. 11 depicts an exemplary embodiment of the present disclosure using UPE imaging for the detection of a breast cancer. FIG. 11A is a 2D UPE image illustration of a female breast cancer hot spot superimposed on a black and white smoothed photo of the patient's torso. The colors represent intensity, using a jet color bar (blue to red). FIG. 11B is an illustration of 3D surface reconstruction of the breasts by using SL data of the torso and applying the surface reconstruction algorithm. FIG. 11C shows the UPE signal reconstruction to the hot spot of the cancer tumor in the breast. The signal reconstruction algorithm uses the 3D surface reconstruction and the UPE imaging as inputs and calculates the spatial origin of the signal deep inside the body. This allows for a better spatial localization of the tumor for follow-up diagnostic and imaging procedures, as well as interventions, the patient is likely to need.

In some embodiments, the instant exemplary embodiments focus on cardiovascular diseases, including but not limited to atherosclerosis, coronary heart disease, ischemic heart disease, hypertension, cardiomyopathies, cardiac hypertrophy, congestive heart failure, peripheral vascular disease, or other. These cardiovascular conditions are highly correlated to oxidative stress. In some embodiments, the instant exemplary embodiments focus on oxidative stress manifested in the heart as a result of an infection, including but not limited to pericarditis, endocarditis, myocarditis, or other. In some embodiments, the exemplary embodiments include measuring all stages of cardiovascular diseases development, including before, during and after any treatment. In some embodiments, UPE signal is an indication of the underlying pathological condition of the cardiovascular disease and can be used to recommend treatment regimen, including but not limited to medication, including but not limited to anticoagulants, aldosterone inhibitors, antiplatelet agents and dual antiplatelet therapy, angiotensin-converting enzyme (ACE) inhibitors, angiotensin II receptor blockers, angiotensin receptor-neprilysin inhibitors, beta blockers, calcium channel blockers, cholesterol-lowering medications, digoxin, digitalis preparations, diuretics, inotropic therapy, Proprotein convertase subtilisin kexin type 9 (PCSK9) inhibitors, vasodilators, anti-inflammatory drugs, minimally invasive operations, including but not limited to anticoagulant therapy, coronary angioplasty, key-hole surgery, robotic surgery, coronary artery bypass grafting, endarterectomy, hybrid therapies, or other. In some embodiments, there would be a correlation of the measured amount of UPE signal in the area of interest of the target area to the at least one recommended treatment regimen for the cardiovascular disease.

FIG. 12 depicts an embodiment of the present exemplary embodiment's application to the UPE image used for the detection of coronary heart disease. The colors represent intensity, using a jet color bar (blue to red). The oxidative stress manifested by the coronary heart disease allows for early detection and intervention to avoid exacerbation and complications of this heart condition.

In some embodiments, the instant exemplary embodiments focus on neurological disorders, including but not limited to stroke, traumatic brain injury, epilepsy, depression and anxiety-related disorders, schizophrenia and bipolar disorder, neurodegenerative diseases, such as Alzheimer's disease, Parkinson's disease, amyotrophic lateral sclerosis, multiple sclerosis, cerebellar ataxia, Huntington's disease, dementia, or other. Oxidative damage has been identified even in early stages of neurodegenerative diseases, indicating that their etiologies are linked to ROS/RNS and oxidative stress. Neuroinflammation and oxidative stress are high correlated with almost all the neurological disorders mentioned. The distribution and progression of oxidative stress in the different neurological disorder varies, enabling the potential for differentiation between the different conditions. In some embodiments, the exemplary embodiments include measuring all stages of neurological disorders' development, including before, during and after any treatment. In some embodiments, UPE signal is an indication of the underlying pathological condition of the neurological disorder and can be used to recommend treatment regimen, including but not limited to medication, including but not limited to analgesics, anesthetics, anorexiants, anticonvulsants, antipyretics, antiemetic/antivertigo agents, antiparkinson agents, anxiolytics, sedatives, and hypnotics, cholinergic agonists, cholinesterase inhibitors, CNS stimulants, drugs used in alcohol dependence, general anesthetics, melatonin, miscellaneous central nervous system agents, muscle relaxants, neuromuscular blockers, neuroprotective agents, parasympathomimetics, psychoactive drugs, sympathomimetics, nervous system drug stubs, VMAT2 inhibitors, or other, surgery, including but not limited to cerebrovascular surgery including aneurysms and arteriovenous malformations (AVMs), and stroke, neuro-oncology, spinal neurosurgery, functional and epilepsy neurosurgery, general neurosurgery, skull base surgery, trigeminal neuralgia and nerve compression syndromes, peripheral nerve injury, deep brain stimulation, radiosurgery, minimally invasive surgery, and complementary treatment including not limited to hyperbaric oxygen treatment, low level light therapy, nutrition, or other. In some embodiments, there would be a correlation of the measured amount of UPE signal in the area of interest of the target area to the at least one recommended treatment regimen for the neurological disorder.

FIGS. 13A-B depict an exemplary embodiment of the present disclosure using UPE imaging for the detection and monitoring of a stroke. FIG. 13A is a 3D UPE image of the head superimposed on a black and white photo of head, retrieved from two cameras. FIG. 13B is the UPE signal reconstruction to the hot spot of the stroke, based on 3D surface reconstruction and the UPE images. The signal reconstruction allows for a spatial localization and better quantification of the stroke associated oxidative stress for detection and monitoring applications. The photo was blurred intentionally for privacy reasons, while still enabling the convenient localization of the stroke hot spot.

In some embodiments, the instant exemplary embodiments focus on arthritis and other rheumatic conditions, including but not limited to osteoarthritis, rheumatoid arthritis, gout, infectious arthritis, juvenile idiopathic arthritis, bursitis, fibromyalgia, polymyalgia rheumatica, polymyositis, scleroderma, systemic lupus erythematosus, tendinitis, or other. These conditions exhibit inflammation and the associated oxidative stress. In some embodiments, the exemplary embodiments include measuring all stages of arthritis and other rheumatic conditions development, including before, during and after any treatment. In some embodiments, UPE signal is an indication of the underlying pathological condition of the arthritis and other rheumatic condition and can be used to recommend treatment regimen including but not limited to medication, including but not limited to nonsteroidal anti-inflammatory drugs, counterirritants, anti-inflammatory drugs, disease-modifying antirheumatic drugs, biologic response modifiers, steroidal drug including but not limited to corticosteroids, Janus Kinase (JAK) inhibitors, or other, surgery, including but not limited to joint repair, replacement, fusion, realigning bones, lubrication injections, transcutaneous electrical nerve stimulation, or other, complementary treatment including but not limited to physical therapy, occupational therapy, low level light therapy, nutrition, or other. In some embodiments, there would be a correlation of the measured amount of UPE signal in the area of interest of the target area to the at least one recommended treatment regimen for the arthritis and other rheumatic condition.

FIGS. 14A-D depict an embodiment of the present disclosure of a hand of a patient suffering from rheumatoid arthritis. FIG. 14A is an UPE image taken without LLLI enhancement, i.e., in a completely passive image acquisition embodiment. FIG. 14B is an UPE image taken after LLLI protocol as part of the exemplary embodiments. The colors represent intensity, using a jet color bar (blue to red). Both images use the same intensity range to illustrate the enhancement of the UPE signal by LLLI. FIG. 14C is a black and white photo of the hand, and FIG. 14D shows a superimposition of the LLLI enhanced UPE image (FIG. 14B) on the black and white photo of the hand (FIG. 14C). Superimposition presentation allows for a more convenient visualization of the arthritis hot spots in the hand.

The efficacy of the administered drug, or other treatments, can be directly observed and/or quantified, and may further allow for better guidance for treatment, such as continuing with the current treatment, changing the dosage or other elements of the treatment, changing the type of treatment, etc. In some embodiments, UPE imaging may allow for longitudinal assessment of the tissue for monitoring the progression of the disease, with the applied treatment.

In some embodiments, UPE imaging can be used for screening of different pathological conditions to allow the application of preventive treatment. For example, in some embodiments, cancerous ovarian tumors are growing and changing the microenvironment; In some embodiments, atherosclerosis is developing into a coronary heart disease; In some embodiments, neuroinflammation is indicative of an early stage of Alzheimer's disease. In some embodiments, UPE imaging can find the hot spots oxidative stress and direct clinical care to those areas. By focusing the follow up diagnostics and treatment to a specific condition, deterioration of these conditions may be avoided. Screening and early treatment increase the effectiveness of treatment, while reducing the likelihood of complications, to enable faster healing.

UPE imaging has some variance based on age, complexion, nutrition, medication, and other factors. The manifestations of every pathological condition also have some variance. The UPE signal associated with different conditions, would change between different individuals and between different stages, of the same condition, even for the same individuals. In some embodiments, in order to establish more universal criteria and improve the algorithms to analyze the UPE images and provide recommendation and guidance for treatment, the method will include a comparison of different patients with similar conditions and with healthy individuals. By comparing and contrasting UPE images of different patients, more generalized behavior of the UPE signal can be assigned to different pathological conditions in different stages of the illness. Comparing and contrasting UPE images of different patients may be done, in the following non-limiting examples, to establish a threshold for hypoxic conditions which precede ulceration, establish a criterion for surgical margins of skin cancer; differentiate between the UPE signal optical and spatial characteristics of inflammation for a properly healing surgical wounds compared to an improperly healing wound; and differentiate between UPE spectral characteristics associated with infection and hypoxic conditions and inflammation. For example, establishing a threshold for the UPE intensity, caused by the non-limiting examples of infection, ischemia or cancerous tumor, would likely lead to better screening procedures.

FIGS. 15A-D depict an exemplary embodiment of the present disclosure used for a control measurement. FIG. 15A shows an UPE measurement of an ulcerated venous stasis wound in the patient's heel that is fully healed. The baseline UPE signal from the patient's heel is visible, with no observable hot spots. FIG. 15B is a RL illumination processed image. FIG. 15C shows a superimposition of the UPE image (FIG. 10A) and the RL illumination image (FIG. 15B). The superimposition illustrated in FIG. 15C, provides better visualization, and allows the user to easily identify the UPE active regions in the area of interest of the target area. This result may be important as a control measurement of true negative. A WL illumination color image in FIG. 15D is presented for reference.

It is appreciated that certain features of the disclosure, which are, for clarity, described in the context of separate embodiments, may also be provided in a single embodiment. Conversely, various features of the disclosure, which are, for brevity, described in the context of a single embodiment, may also be provided separately or in any suitable sub combination or as suitable in any other described embodiment of the disclosure. Certain features described in the context of various embodiments are not considered essential features of these embodiments, unless the embodiment is inoperative without those elements.

What is claimed:

1. A method, comprising:
   acquiring an ultraweak photon emission image of a target area of a patient for detection of a pathological condition;
   wherein the target area comprises an area of interest and a portion surrounding the area of interest,
   wherein acquiring the image comprises:
   enhancing formation of reactive oxygen species (ROS) and/or reactive nitrogen species (RNS) in the target area,
   wherein enhancing formation of the ROS and/or the RNS comprises applying low level light illumination to the target area from 1 second to 60 minutes so as to
   achieve a total power output from 1 mW to 10,000 W using an average power density from 0.1 W/cm$^2$ to 1 W/cm$^2$, and
   create an enhanced amount of ROS and/or RNS caused by the applied low level light illumination in the target area; and
   imaging the target area when at least a portion of the enhanced amount of ROS and/or RNS caused by the applied low level light illumination is present in the target area,
   wherein imaging the target area comprises a total exposure time from 1 second to 60 minutes.

2. The method of claim 1, wherein applying low level light illumination comprises using a plurality of illumination sources.

3. The method of claim 1, wherein applying low level light illumination comprises applying a continuation light wave.

4. The method of claim 1, wherein applying low level light illumination comprises applying a pulsed light wave.

5. The method of claim 1, wherein the low level light illumination comprises wavelengths from 600 nm to 1100 nm.

6. The method of claim 1, further comprising applying red light illumination to the target area from 1 second to 5 minutes.

7. The method of claim 1, further comprising applying white light illumination to the target area from 1 second to 1 minute.

8. The method of claim 1, wherein enhancing formation of the reactive oxygen species and/or the reactive nitrogen species in the target area comprises applying cryotherapy, thermal therapy, fluidotherapy, hydrotherapy, ultrasound, heat lamp, diathermy, or any combination thereof to the target area.

* * * * *